United States Patent
Wang et al.

(10) Patent No.: US 10,543,199 B2
(45) Date of Patent: Jan. 28, 2020

(54) MACROCYCLE AND COMPOSITION COMPRISING THEREOF

(71) Applicant: Shenzhen TargetRx, Inc., Shenzhen (CN)

(72) Inventors: Yihan Wang, Shenzhen (CN); Huanyin Li, Shenzhen (CN)

(73) Assignee: Shenzhen TargetRx, Inc., Shenzhen, Guangdong (CN)

( * ) Notice: Subject to any disclaimer, the term of this patent is extended or adjusted under 35 U.S.C. 154(b) by 0 days.

(21) Appl. No.: 16/081,611

(22) PCT Filed: Feb. 23, 2017

(86) PCT No.: PCT/CN2017/074555
§ 371 (c)(1),
(2) Date: Aug. 31, 2018

(87) PCT Pub. No.: WO2017/148325
PCT Pub. Date: Sep. 8, 2017

(65) Prior Publication Data
US 2019/0060292 A1    Feb. 28, 2019

(30) Foreign Application Priority Data

Mar. 3, 2016 (CN) .......................... 2016 1 0117814

(51) Int. Cl.
*A61K 45/06* (2006.01)
*A61K 31/439* (2006.01)
*A61K 35/00* (2006.01)
*A61P 35/00* (2006.01)

(52) U.S. Cl.
CPC ............ *A61K 31/439* (2013.01); *A61K 45/06* (2013.01); *A61P 35/00* (2018.01)

(58) Field of Classification Search
CPC ......... A61P 31/439; A61P 35/00; A61K 45/06
USPC ....................................................... 514/286
See application file for complete search history.

(56) References Cited

FOREIGN PATENT DOCUMENTS

| | | |
|---|---|---|
| CN | 104169286 | 11/2014 |
| CN | 104513253 A | 4/2015 |
| EP | 2822953 B9 | 2/2017 |
| JP | 2014-005265 A | 1/2014 |
| JP | 2014-526524 A | 10/2014 |
| JP | 2015-010091 A | 1/2015 |
| JP | 2015-510879 A | 4/2015 |
| WO | 2014207606 | * 12/2014 |
| WO | WO 2014/207606 A1 | 12/2014 |

OTHER PUBLICATIONS

PCT/CN2017/074555, May 27, 2017, International Search Report and Written Opinion.
PCT/CN2017/074555, Sep. 13, 2018, International Preliminary Report on Patentability.
Jiang et al., Application of deuteration in drug research. Qilu Pharmaceutical Affairs. 2010;29(11):682-684.
Japanese Office Action for Application No. JP 2018-545928 dated Aug. 27, 2019.

* cited by examiner

Primary Examiner — Niloofar Rahmani
(74) Attorney, Agent, or Firm — Wolf, Greenfield & Sacks, P.C.

(57) ABSTRACT

A macrocycle represented by formula (I) and a pharmaceutical composition comprising the macrocycle, or a crystalline form, pharmaceutically acceptable salt, hydrate or solvent compound, stereoisomer, prodrug, or isotopic variant of the macrocycle. The macrocycle and the composition thereof inhibit a protein kinase.

16 Claims, No Drawings

MACROCYCLE AND COMPOSITION COMPRISING THEREOF

CROSS REFERENCE TO RELATED APPLICATIONS

This application is a national stage filing under 35 U.S.C. § 371 of International Application Serial No. PCT/CN2017/074555, filed Feb. 23, 2017, entitled "MACROCYCLE AND COMPOSITION COMPRISING THEREOF", which claims the benefit of priority to Chinese Patent Application Serial No. 201610117814.2, filed Mar. 3, 2016, the entire contents of each of which are incorporated by reference herein.

FIELD OF THE INVENTION

The present disclosure belongs to the pharmaceutical field, and in particular relates to a macrocyclic compound and a composition comprising the same.

BACKGROUND OF THE INVENTION

In the past 30 years, the mortality rate of lung cancer has risen by 465%, and the incidence rate has increased by 26.9% annually. It has become the first cause of death from malignant tumors in China. Among them, non-small cell lung cancer (NSCLC) accounts for greater than 80% of all lung cancers. Only one third of NSCLC patients have the opportunity of surgical treatment, and about 70% of patients have been locally advanced or had distant metastasis before seeing a doctor, and lost the chance of surgery. In this case, drug treatment seems particularly important. The anaplastic lymphoma kinase (ALK) gene fusion has recently become an important biomarker, which helps the identification of patients with specific NSCLC subgroup and thereby the choice of the corresponding inhibitors for treatment. The International Association for the Study of Lung Cancer (IASLC) recommends the use of ALK fusion testing to guide the patient screening and select from patients with advanced adenocarcinoma who can be treated with an ALK inhibitor regardless of gender, race, smoking history, or other clinical risk factors. Fluorescence in situ hybridization (FISH) using a dual-label separation probe is used for the selection of patients who can receive ALK-TKI therapy. This diagnostic method was approved by the US FDA and has been adopted in the study of the treatment of ALK rearranged tumors with crizotinib. Crizotinib is an oral adenosine triphosphate (ATP) competitive inhibitor that can inhibit ALK and MET tyrosine kinases and also inhibit the activity of ROS1 and RON kinase.

However, crizotinib has the following side effects: visual disturbances, gastrointestinal side effects, and 3-4 level of hepatic aminotransferase increase in 16% of cases. In addition, ALK-positive patients inevitably acquired resistance after a sensitive period of crizotinib treatment at the initial stage. Thus, there is a need to develop compounds that have ALK kinase inhibitory activity and/or have better pharmacodynamic/pharmacokinetic properties.

SUMMARY OF THE INVENTION

In view of the above technical problems, disclosed herein are a macrocyclic compound and a composition comprising the same, which have better inhibitory activity for ALK kinase and/or have better pharmacodynamic/pharmacokinetic properties.

In this regard, the technical solution adopted herein is:

The object of the present disclosure is to provide a new class of compounds having inhibitory activity for ALK kinase and/or having better pharmacodynamic/pharmacokinetic properties.

In a first aspect, disclosed herein is a macrocyclic compound represented by Formula (I), or a crystalline form, a pharmaceutically acceptable salt, a prodrug, a stereoisomer, a hydrate or a solvate thereof.

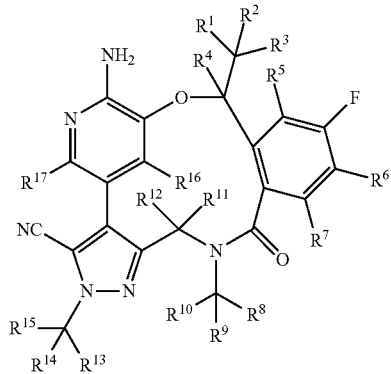

Formula (I)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are each independently hydrogen, deuterium, or halogen;

provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ is deuterated or deuterium.

In another embodiment, $R^1$, $R^2$, and $R^3$ are each independently deuterium or hydrogen.

In another embodiment, $R^4$ is deuterium or hydrogen.

In another embodiment, $R^5$, $R^6$ and $R^7$ are each independently deuterium or hydrogen.

In another embodiment, $R^8$, $R^9$, $R^{10}$, $R^{11}$, $R^{12}$, $R^{13}$, $R^{14}$, and $R^{15}$ are each independently deuterium or hydrogen.

In another embodiment, $R^{16}$ and $R^{17}$ are each independently deuterium or hydrogen.

In another embodiment, the compound is selected from, but not limited to, the group consisting of the following compounds, or pharmaceutically acceptable salts thereof:

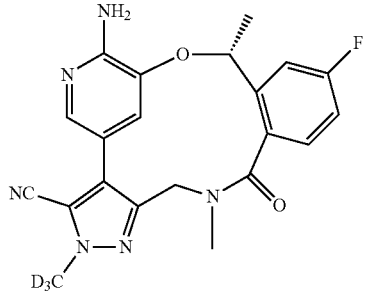

Formula (2)

-continued
Formula (3)
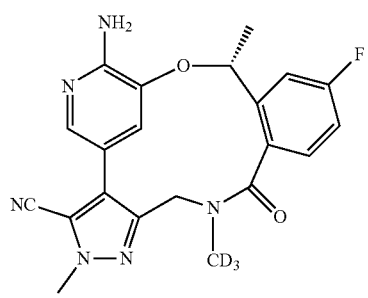
Formula (4)
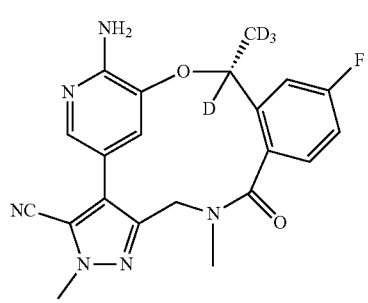
Formula (5)
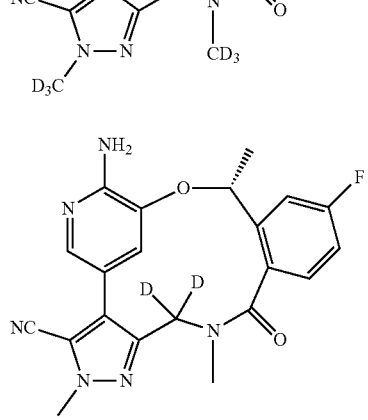
Formula (6)
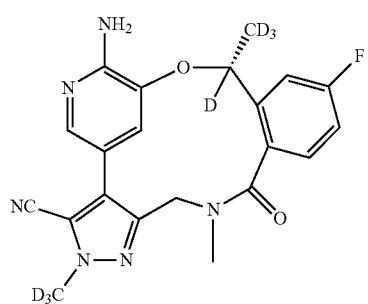
Formula (7)
Formula (8)
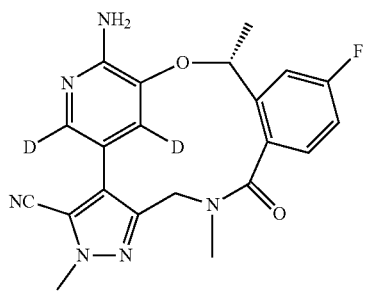
Formula (9)
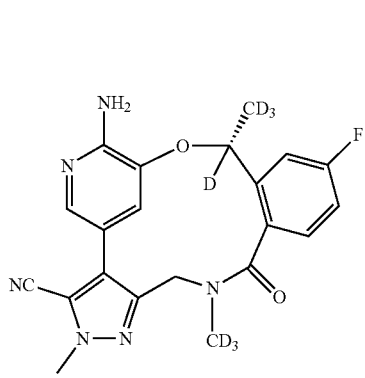
Formula (10)
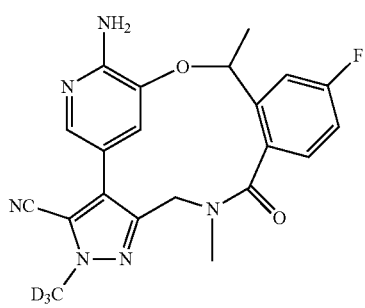
Formula (11)
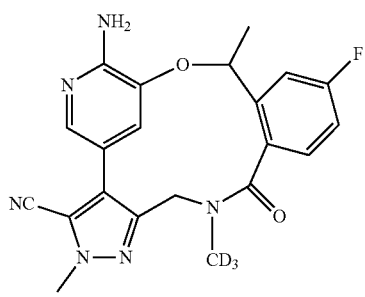
Formula (12)
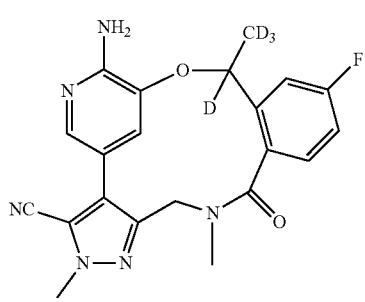

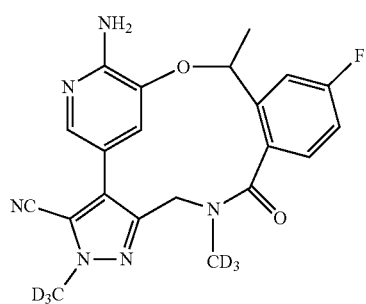
Formula (13)
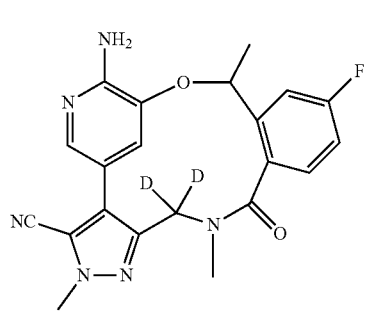
Formula (14)
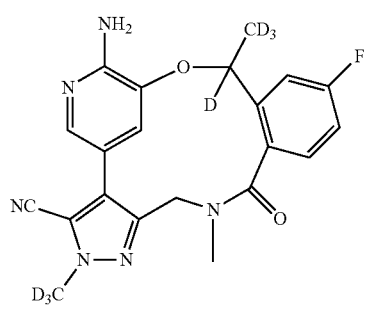
Formula (15)
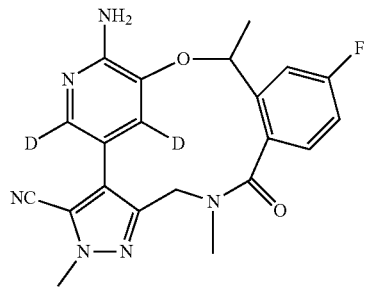
Formula (16)
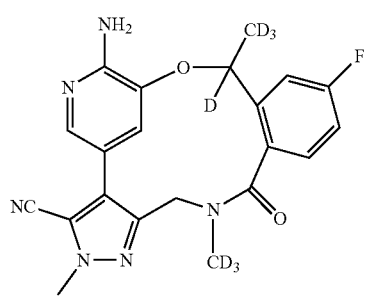
Formula (17)
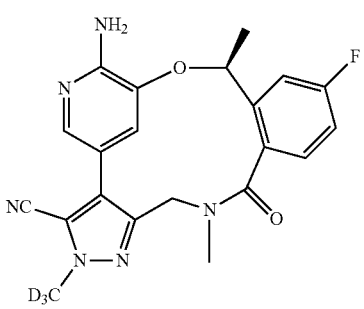
Formula (18)
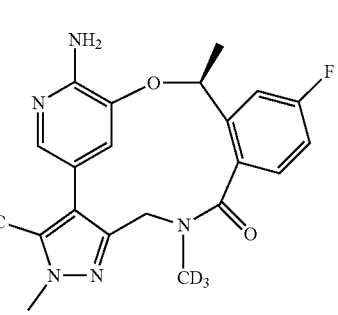
Formula (19)
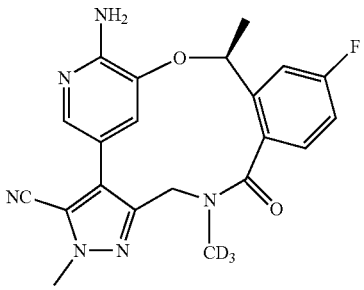
Formula (20)
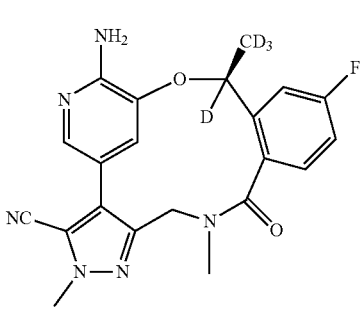
Formula (21)
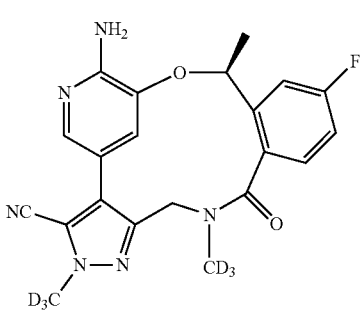
Formula (22)
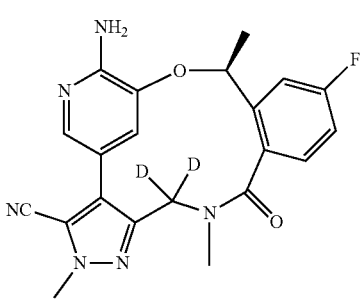

Formula (23)
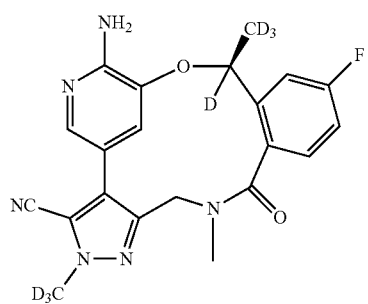
Formula (24)
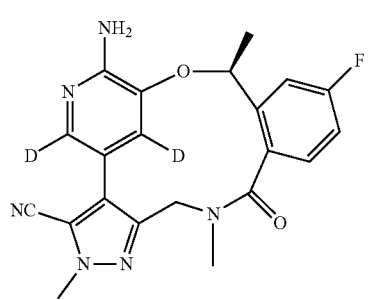
Formula (25)
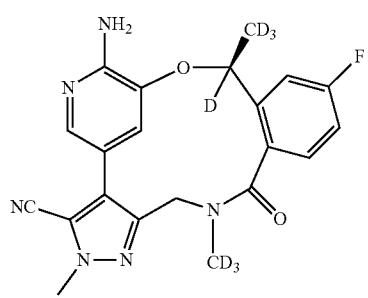
Formula (26)
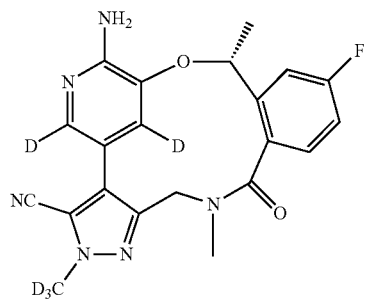
Formula (27)
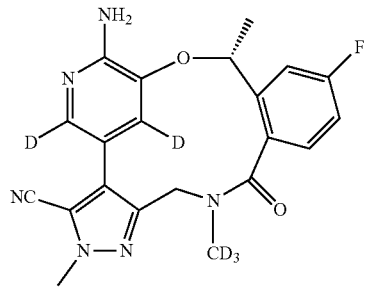
Formula (28)
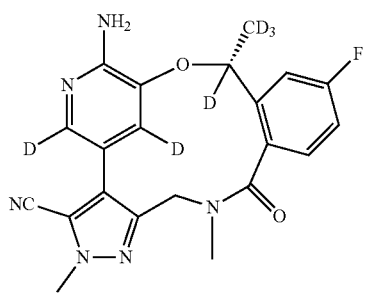
Formula (29)
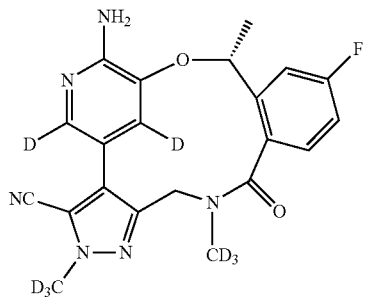
Formula (30)
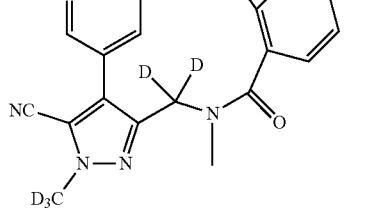
Formula (31)
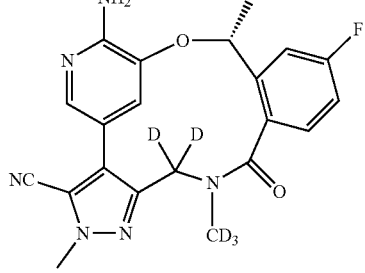
Formula (32)
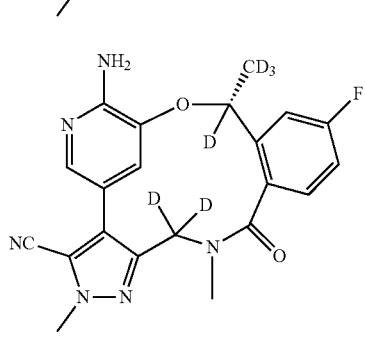

-continued

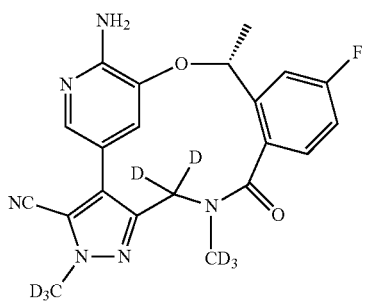
Formula (33)

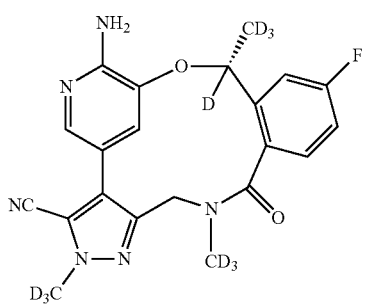
Formula (34)

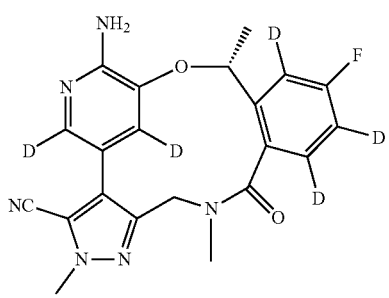
Formula (35)

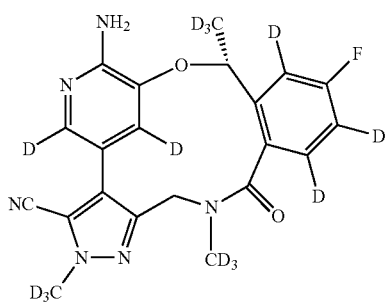
Formula (36)

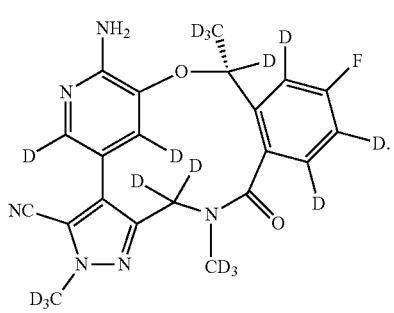
Formula (37)

The shape and volume of deuterium in a drug molecule is essentially the same as that of hydrogen. If hydrogen in a drug molecule is selectively replaced with deuterium, deuterated drugs generally retain their original biological activity and selectivity. At the same time, the inventors confirmed through experiments that the binding of carbon-deuterium bonds is more stable than the binding of carbon-hydrogen bonds, which can directly affect the properties such as absorption, distribution, metabolism, and excretion of some drugs, thereby improving the efficacy, safety, and tolerability of drugs.

In another embodiment, the content of deuterium isotope in each deuterated position is at least greater than the natural content of deuterium isotope (0.015%), preferably greater than 30%, more preferably greater than 50%, more preferably greater than 75%, more preferably greater than 95%, and more preferably greater than 99%.

Specifically, in the present disclosure, the content of the deuterium isotope in each deuterated position of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ is at least 5%, preferably greater than 10%, more preferably greater than 15%, more preferably greater than 20%, more preferably greater than 25%, more preferably greater than 30%, more preferably greater than 35%, more preferably greater than 40%, more preferably greater than 45%, more preferably greater than 50%, more preferably greater than 55%, more preferably greater than 60%, more preferably greater than 65%, more preferably greater than 70%, more preferably greater than 75%, more preferably greater than 80%, more preferably greater than 85%, more preferably greater than 90%, more preferably greater than 95%, and more preferably greater than 99%.

In another embodiment, in $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ in the compound of formula (I), at least one R contains deuterium, and more preferably two Rs, more preferably three Rs, more preferably four Rs, more preferably five Rs, more preferably six Rs, more preferably seven Rs, more preferably eight Rs, more preferably nine Rs, more preferably ten Rs, and more preferably eleven Rs, more preferably twelve Rs, more preferably thirteen Rs, more preferably fourteen Rs, more preferably fifteen Rs, more preferably sixteen Rs, and more preferably seventeen Rs contain deuterium.

In another embodiment, the compound does not include a non-deuterated compound.

In the second aspect, disclosed herein is a method for preparing a pharmaceutical composition comprising the step of mixing a pharmaceutically acceptable carrier with the compound as described in the first aspect disclosed herein, or a crystal form, a pharmaceutically acceptable salt, a hydrate or a solvate thereof to form a pharmaceutical composition.

In a third aspect, disclosed herein is a pharmaceutical composition comprising a pharmaceutically acceptable carrier and a compound as described in the first aspect disclosed herein, or a crystalline form, a pharmaceutically acceptable salt, a hydrate or a solvate thereof.

In another embodiment, the pharmaceutical composition is an injection, sachet, tablet, pill, powder, or granule.

In another embodiment, the pharmaceutical composition further comprises an additional therapeutic drug, which is a drug for cancer, cardiovascular disease, inflammation, infection, immune disease, cell proliferative disease, viral disease, metabolic disease, or organ transplant.

In a fourth aspect, disclosed herein is use of a compound as described in the first aspect disclosed herein, or a crystalline form, a pharmaceutically acceptable salt, a prodrug, a stereoisomer, an isotopic variant, a hydrate or a solvent thereof in the preparation of a pharmaceutical composition for inhibiting protease.

In another embodiment, the pharmaceutical composition is used to treat and prevent the following diseases: cancer, cell proliferative disease, inflammation, infection, immune disease, organ transplantation, viral disease, cardiovascular disease or metabolic diseases.

In another embodiment, the cancer includes but is not limited to lung cancer, head and neck cancer, breast cancer, prostate cancer, esophageal cancer, rectal cancer, colon cancer, nasopharyngeal cancer, uterine cancer, pancreatic cancer, lymphoma, blood cancer, osteosarcoma, melanoma, kidney cancer, stomach cancer, liver cancer, bladder cancer, thyroid cancer, or large intestine cancer.

In another embodiment, the immune disease or inflammation includes but is not limited to: rheumatoid arthritis, osteoarthritis, rheumatoid spondylitis, gout, asthma, bronchitis, rhinitis, chronic obstructive pulmonary disease, and cystic fibrosis.

In another embodiment, the cell proliferative disease refers to lung cancer, head and neck cancer, breast cancer, prostate cancer, esophageal cancer, rectal cancer, colon cancer, nasopharyngeal cancer, uterine cancer, pancreatic cancer, lymphoma, blood cancer, osteosarcoma, melanoma, kidney cancer, stomach cancer, liver cancer, bladder cancer, thyroid cancer, or large intestine cancer.

In another embodiment, the cancer is non-small cell lung cancer.

In a fifth aspect, disclosed herein is a method for inhibiting a protein kinase (such as ALK kinase) or a method for treating a disease (such as cancer, cell proliferative disease, inflammation, infection, immune disease, organ transplantation, viral disease, cardiovascular disease or metabolic disease), which comprises the step of administering to a subject in need of treatment a compound as described in the first aspect disclosed herein, or a crystalline form, a pharmaceutically acceptable salt, a hydrate or a solvent thereof, or a pharmaceutical composition as described in the third aspect disclosed herein.

It should be understood that within the scope disclosed herein, the above technical features disclosed herein and the technical features specifically described in the following (such as the examples) can be combined with each other to constitute a new or preferred technical solution. Due to space limitations, such technical solution will not be repeated herein.

Also disclosed herein are isotopically labeled compounds to the extent of the original compounds disclosed herein. Examples of isotopes that can be listed as compounds disclosed herein include hydrogen, carbon, nitrogen, oxygen, phosphorus, sulfur, fluorine, and chlorine isotopes, such as $^2$H, $^3$H, $^{13}$C, $^{14}$C, $^{15}$N, $^{17}$O, $^{18}$O, $^{31}$P, $^{32}$P, $^{35}$S, $^{18}$F, and $^{36}$Cl, respectively. Compounds disclosed herein, or enantiomers, diastereomers, isomers, or pharmaceutically acceptable salts or solvates thereof, in which the isotopes as described above or other isotope atoms are contained, are within the scope disclosed herein. Certain isotopically labeled compounds disclosed herein, such as the radioisotopes of $^3$H and $^{14}$C, are also among them and are useful in the tissue distribution experiments of drugs and substrates. Tritium, i.e., $^3$H, and carbon-14, i.e., $^{14}$C, are easier to prepare and detect and are the first choice for isotopes. In addition, substitution with heavier isotopes such as deuterium, i.e., $^2$H, has advantages in some therapies due to its good metabolic stability, for example, increased half-life in vivo or reduced dosage, and thus priority may be given in some cases. Isotopically-labeled compounds can be prepared using the schemes shown in the Examples by conventional methods by replacing the non-isotopic reagents with readily available isotopically labeled reagents.

Herein, "halogen" means F, Cl, Br, and I unless otherwise specified. More preferably, a halogen atom is selected from F, Cl and Br.

Herein, unless otherwise specified, "$C_1$-$C_6$ alkyl" means a linear or branched alkyl group including 1 to 6 carbon atoms, such as methyl, ethyl, propyl, isopropyl, butyl, isobutyl, tert-butyl, or the like.

Herein, unless otherwise specified, "deuterated" means that one or more hydrogens in a compound or group are replaced by deuterium; the "deuterated" may be mono-substituted, di-substituted, multi-substituted or fully substituted. The terms "substituted with one or more deuteriums" and "substituted by one or more deuteriums" are used interchangeably.

Herein, unless otherwise specified, "non-deuterated compound" means a compound containing deuterium in a ratio that is not higher than the natural content of deuterium isotope (0.015%).

In the present disclosure, pharmaceutically acceptable salts include inorganic and organic salts. A preferred class of salts is the salt formed by the compound disclosed herein with an acid. Acids suitable for formation of salts include, but are not limited to: inorganic acids such as hydrochloric acid, hydrobromic acid, hydrofluoric acid, sulfuric acid, nitric acid, phosphoric acid; organic acids such as formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, p-toluenesulfonic acid, benzenesulfonic acid, naphthalenesulfonic acid; amino acids such as proline, phenylalanine, aspartic acid, and glutamic acid. Another preferred class of salt is a salt of a compound disclosed herein with a base such as an alkali metal salt (e.g., sodium or potassium salt), an alkaline earth metal salt (e.g., magnesium salt or calcium salt), an ammonium salt (e.g., a lower alkanolammonium salt and other pharmaceutically acceptable amine salts) such as methylamine salt, ethylamine salt, propylamine salt, dimethylamine salt, trimethylamine salt, diethylamine salt, triethylamine salt, tert-butylamine salt, ethylenediamine salt, hydroxyethylamine salt, dihydroxyethylamine salt, triethanolamine salt, and amine salts formed from morpholine, piperazine, and lysine, respectively.

The term "solvate" refers to a complex in which a compound disclosed herein coordinates with a solvent molecule in a particular ratio. "Hydrate" refers to a complex formed by coordination of a compound disclosed herein with water.

Compared with the prior art, the beneficial effects disclosed herein are that the compounds disclosed herein have excellent inhibitory properties against protein kinases such as ALK kinases. The deuteration technology alters the metabolism of the compound in the organism, allowing the compound to have better pharmacokinetic parameters. In this case, the dose can be changed and a long-acting formulation can be formed to improve the applicability. The use of deuterium to replace hydrogen atoms in compounds can increase the drug concentration of the compound in animals due to its deuterium isotope effect, so as to improve the efficacy of the drug. The replacement of hydrogen atoms in compounds with deuterium may increase the safety of the compounds due to the inhibition of certain metabolites.

DETAILED DESCRIPTION OF THE EMBODIMENTS

The method for preparing the compounds of the Formula (I) according to the present disclosure will be more specifically described below, but these specific methods do not impose any limitations on the present disclosure. The compounds disclosed herein can also be conveniently prepared by combining various synthesis methods described in this specification or known in the art, and such combinations can be easily performed by those skilled in the art to which the present disclosure pertains.

In general, in a preparation process, each reaction is usually carried out in an inert solvent at room temperature to reflux temperature (e.g., 0° C. to 100° C., preferably 0° C. to 80° C.). The reaction time is usually 0.1 to 60 hours, preferably 0.5 to 24 hours.

The following detailed description will be given in conjunction with the examples.

Example 1 Synthesis of Intermediate methyl 2-(1-((2-amino-5-bromopyridin-3-yl)oxy)ethyl)-4-fluorobenzoate (Compound 7)

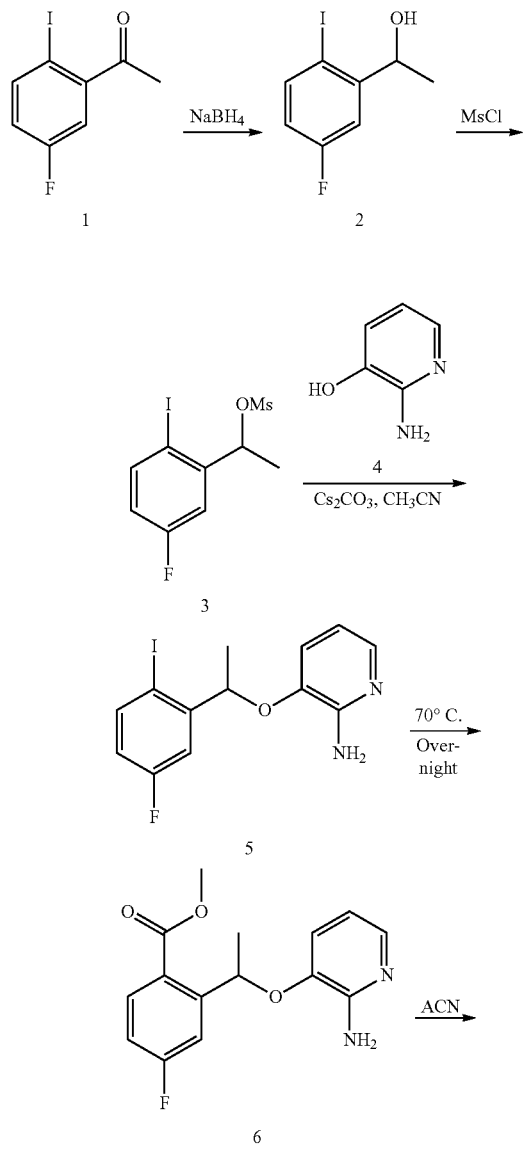

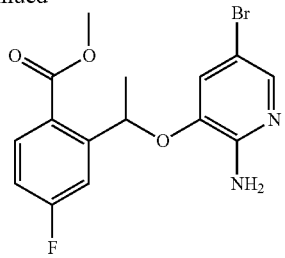

Step 1 Synthesis of Compound 2.

Under a nitrogen atmosphere, a solution of compound 1 (2.6 g, 10 mmol) in methanol (50 mL) was cooled in an ice-water bath, into which NaBH$_4$ (0.38 g, 10 mmol) was poured slowly, and continued to react at 0° C. for 5 minutes. 0.5M HCl solution was added dropwise slowly until no bubbles appeared in the reaction system. The reaction solution was adjusted to pH>7 with saturated sodium bicarbonate solution, and extracted with ethyl acetate to obtain 2.6 g of a white solid product with a yield of 99%. LC-MS (APCI): m/z=267 (M+1)$^+$; $^1$H NMR (300 MHz, CDCl$_3$)(δ ppm) 7.76-7.71 (m, 1H), 7.35-7.31 (m, 1H), 6.78-6.72 (m, 1H), 5.05-4.99 (m, 1H), 1.45 (d, J=6.0 Hz, 3H).

Step 2 Synthesis of Compound 3.

Et$_3$N (1.52 g, 15 mmol) and MsCl (1.5 g, 13 mmol) were sequentially added to a solution of compound 2 (2.6 g, 10 mmol) in dichloromethane (60 mL) at 0° C. After the addition was completed, the reaction mixture was stirred at room temperature. After stirring for 1 hour, water and dichloromethane were added. The organic phase was separated, washed successively with water, 0.5 M HCl solution, and saturated sodium bicarbonate solution, and dried over anhydrous sodium sulfate to give 3.1 g of a light-colored solid product which was directly used for the next step. LC-MS (APCI): m/z=345 (M+1)$^+$.

Step 3 Synthesis of Compound 5.

Compound 4 (0.48 g, 4.3 mmol) and cesium carbonate (1.9 g, 5.8 mmol) were sequentially added to a solution of compound 3 (1.0 g, 2.9 mmol) in acetonitrile (50 mL) and heated to 85° C. for 2 hours. The mixture was cooled to room temperature, diluted with ethyl acetate, and filtered. The filtrate was collected and purified by column to give a light-colored solid product (500 mg) with a yield of 48%. LC-MS (APCI): m/z=359.1 (M+1)$^+$; $^1$H NMR (300 MHz, DMSO-d$_6$)(δ ppm) 7.90-7.85 (m, 1H), 7.47-7.45 (m, 1H), 7.40-7.35 (m, 1H), 7.00-6.94 (m, 1H), 6.57 (d, J=7.8 Hz, 1H), 6.40-6.35 (m, 1H), 5.90 (brs, 2H), 5.40 (q, J=6.3 Hz, 1H), 1.54 (d, J=6.3 Hz, 3H).

Step 4 Synthesis of Compound 6.

Pd(dppf)Cl$_2$ (102 mg, 0.14 mmol) and Et$_3$N (140 mg, 1.4 mmol) were sequentially added to a solution of compound 5 (0.25 g, 0.7 mmol) in MeOH (5 mL). The reaction system was evacuated and CO was bubbled through. The reaction was carried out at 70° C. overnight in a CO atmosphere. After cooling to room temperature, ethyl acetate was added and the mixture was filtered. The filtrate was collected and purified by column to obtain 150 mg of a white product with a yield of 73%. LC-MS (APCI): m/z=291.1 (M+1)$^+$; $^1$H NMR (300 MHz, CDCl$_3$)(δ ppm) 8.05-8.03 (m, 1H), 7.61-7.58 (m, 1H), 7.30-7.27 (m, 1H), 7.00-6.95 (m, 1H), 6.61 (d, J=8.1 Hz, 1H), 6.42 (d, J=8.1 Hz, 1H), 6.33-6.30 (m, 1H), 4.75 (br s, 2H), 3.95 (s, 3H), 1.65 (d, J=6.3 Hz, 3H).

Step 5 Synthesis of Compound 7.

Under a nitrogen atmosphere, compound 6 (440 mg, 1.5 mmol) and acetonitrile (6 mL) were successively added to a stirred single-neck flask. The reaction system was cooled to 0° C., and a solution of N-bromosuccinimide (NBS, 267 mg, 1.5 mmol) in acetonitrile (6 mL) was added dropwise and the reaction was continued for 15 minutes. The solvent was removed by rotary evaporation. The residue was dissolved in ethyl acetate and washed successively with NaOH, 10% aqueous sodium thiosulfate and dried over anhydrous sodium sulfate. The organic phases were collected and purified by column to obtain 400 mg of a brown oily product with a yield of 71%. LC-MS (APCI): m/z=369.1 (M+1)$^+$; $^1$H NMR (300 MHz, CDCl$_3$)(δ ppm) 8.07-8.05 (m, 1H), 7.68-7.65 (m, 1H), 7.26-7.24 (m, 1H), 7.04-7.02 (m, 1H), 6.75 (d, J=8.1 Hz, 1H), 6.33-6.30 (m, 1H), 4.77 (br s, 2H), 3.97 (s, 3H), 1.65 (d, J=6.3 Hz, 3H).

Example 2 Preparation of Substituted Macrocyclic Compound 18

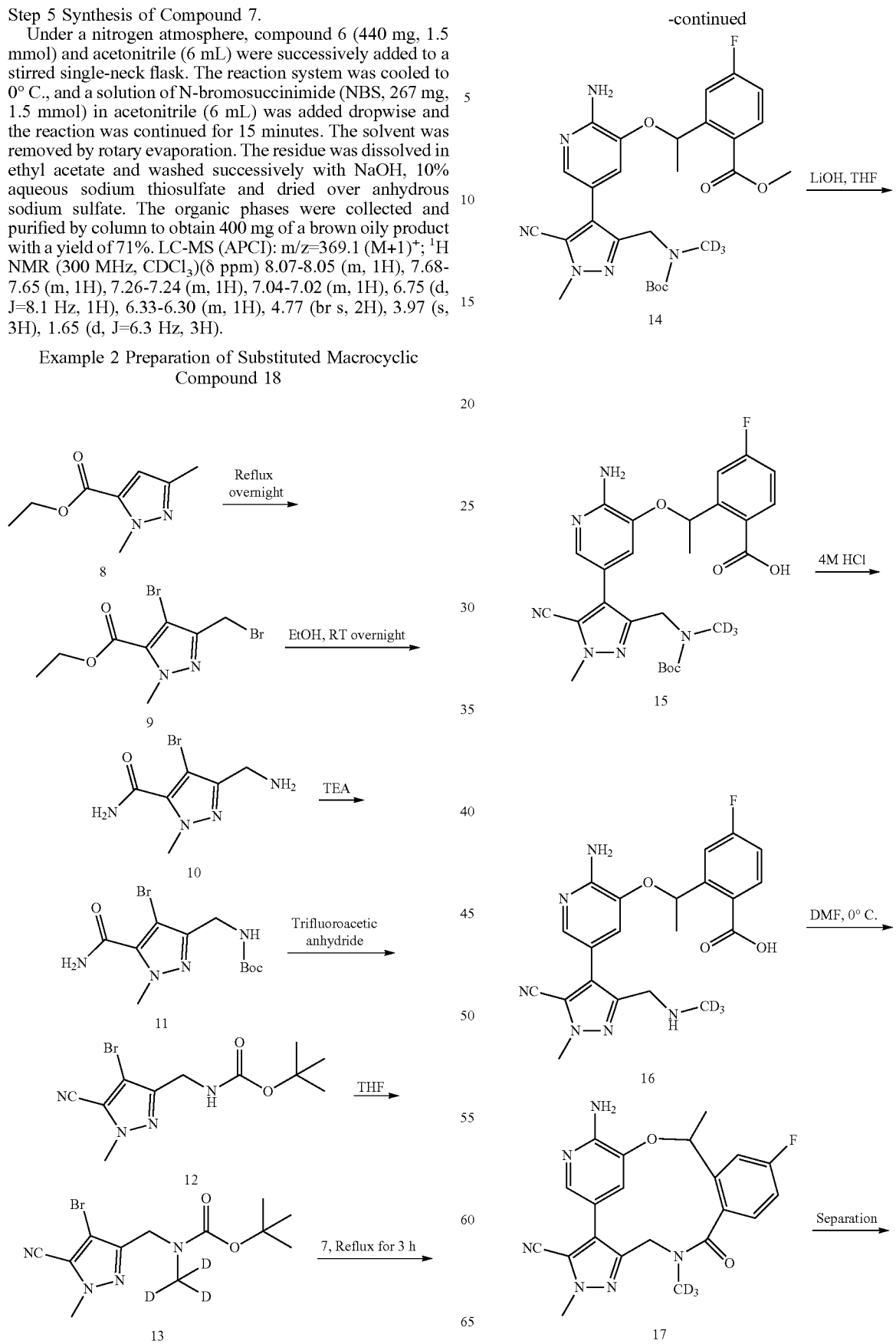

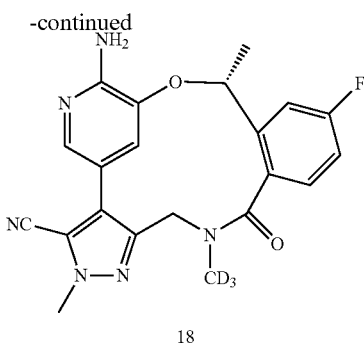

18

Step 1 Synthesis of Compound 9.

Compound 8 (6.72 g, 40 mmol) and 1,2-dichloroethane (100 mL) was added to a single-neck flask to give a clear solution, and to the stirred solution was added NBS (14.92 g, 84 mmol), and benzoyl peroxide (BPO, 1.24 g, 5.2 mmol). The mixture was heated to reflux overnight, then cooled to room temperature and stirred in an ice bath for 1 hour. After a needle solid appeared, it was filtered, and the filtrate was collected and purified by column to give 9.1 g of a white solid with a yield of 70%. LC-MS (APCI): m/z=327 $(M+1)^+$; $^1$H NMR (300 MHz, $CDCl_3$)(δ ppm) 4.48 (s, 2H), 4.41 (q, J=5.4 Hz, 2H), 4.14 (s, 3H), 1.41 (t, J=5.4 Hz, 3H).

Step 2 Synthesis of Compound 10.

Compound 9 (2 g, 6.13 mmol) and ethanol (15 ml) were added to a single-neck flask. After a clear solution was formed, an aqueous ammonia (15 ml) was added. The mixture was stirred at room temperature for 24 hours and concentrated to give 1.5 g of a yellow solid, which was used directly for the next step. LC-MS (APCI): m/z=233 $(M+1)^+$.

Step 3 Synthesis of Compound 11.

Compound 10 (1.5 g, 6.13 mmol), N,N-dimethylformamide (DMF, 40 mL) and triethylamine (TEA, 1.3 g, 13 mmol) were successively added in a continuously stirred two-neck round bottom flask. After the addition of dichloromethane, the reaction system was placed under a nitrogen atmosphere. $(BOC)_2O$ (2 g, 9 mmol) was added dropwise in an ice-water bath, and the mixture was stirred at room temperature overnight. The reaction was quenched with water and dichloromethane. The mixture was extracted with dichloromethane. The organic phase was separated and purified by column to give 600 mg of a white solid product with a yield of 29%. LC-MS (APCI): m/z=333 $(M+1)^+$.

Step 4 Synthesis of Compound 12.

In a continuously stirred three-neck round-bottom flask, compound 11 (1.2 g, 3.6 mmol), dichloromethane (90 mL) and TEA (2.9 g, 28.8 mmol) were successively added, and cooled to −5° C. A solution of trifluoroacetic anhydride (3.8 mg, 18 mmol) in dichloromethane (10 mL) was added dropwise and stirred at 0° C. for 1 hour. The mixture was diluted with dichloromethane, and washed successively with 5% citric acid, sodium bicarbonate solution, and brine. The organic phase was collected and purified by column to give 790 mg of a yellow solid with a yield of 70%. LC-MS (APCI): m/z=315.1 $(M+1)^+$.

Step 5 Synthesis of Compound 13.

Under a nitrogen atmosphere, compound 12 (460 mg, 1.5 mmol) was added to a two-neck round-bottom flask and tetrahydrofuran (5 mL) was added to give a clear solution which was cooled to −78° C. Hexamethyldisilazide lithium (LiHMDS, 1.7 ml, 1.7 mmol) was added. After stirring for 30 minutes, $CD_3I$ (283 mg, 1.95 mmol) was added, and the mixture was stirred at room temperature for 3 hours after the addition was completed. After adding water and extracting with ethyl acetate, the organic phase was collected and purified by column to give 230 mg of a yellow oily product with a yield of 48%. LC-MS (APCI): m/z=332.1 $(M+1)^+$.

Step 6 Synthesis of Compound 14.

Under a nitrogen atmosphere, compound 7 (90 mg, 0.24 mmol), compound 13 (100 mg, 0.3 mmol), bis-pinacol diboron (90 mg, 0.36 mmol), CsF (190 mg, 1.26 mmol) and $MeOH/H_2O$ (9:1, 5 mL) were successively added to a two-neck round bottom flask. After uniform stirring, a solution of $Pd(OAc)_2$ (3 mg, 0.013 mmol) in toluene (0.5 mL) was added and heated to 60° C. After refluxing overnight, the mixture was cooled to room temperature, diluted with ethyl acetate, and filtered. The filtrate was washed successively with water and brine. The organic phase was collected and purified by column to give 87 mg of a yellow oily product with a yield of 67%. LC-MS (APCI): m/z=542.2 $(M+1)^+$.

Step 7 Synthesis of Compound 15.

To a single-neck round bottom flask was sequentially added compound 14 (200 mg, 0.36 mmol), tetrahydrofuran (20 mL), $LiOH \cdot H_2O$ (151 mg, 3.6 mmol) and $H_2O$ (5 mL), and stirred overnight at room temperature. Sodium sulfate decahydrate was added, and stirred for 5 minutes. The mixture was dried over anhydrous sodium sulfate and filtered. The organic phase was collected to afford 180 mg of a brown oily product with a yield of 95%. LC-MS (APCI): m/z=528 $(M+1)^+$.

Step 8 Synthesis of Compound 16.

Under a nitrogen atmosphere, compound 15 (180 mg, 0.34 mmol), MeOH (2 mL), and HCl in 1,4-dioxane (2 mL, 3.32 mmol) were added sequentially to a single-neck round bottom flask and heated to 40° C. The mixture was reacted for 2 hours. The solvent was removed, and the residue was purified by column to give 80 mg of a yellow oily product with a yield of 53%. LC-MS (APCI): m/z=428.2 $(M+1)^+$.

Step 9 Synthesis of Compound 18.

2-(7-azobenzotriazole)-N,N,N',N'-tetramethyluronium hexafluorophosphate (HATU, 97 mg, 0.25 mmol) and dry DMF (2 mL) was added sequentially to a single-neck round bottom flask, and cooled to 0° C. Then, a mixed solution of compound 16 (80 mg, 0.18 mmol) and N,N-diisopropylethylamine (DIPEA, 234 mg, 1.4 mmol) in DMF (1 mL) and THF (0.1 mL) was slowly added dropwise into the above round bottom flask at 0° C. After the addition was completed, stirring was continued at this temperature for 30 minutes. After adding water and ethyl acetate to quench the reaction, the organic phase was separated, and extracted with ethyl acetate. The organic phase was collected and purified by column to obtain 20 mg of a white solid compound 17. The racemate compound 17 (20 mg) was separated using a chiral supercritical fluid chromatography (SFC) to give the target products R-18 and S-18, 6 mg each. LC-MS (APCI): m/z=410 $(M+1)^+$; $^1$H NMR (300 MHz, $CDCl_3$)(δ ppm) 7.75 (s, 1H), 7.24-7.11 (m, 2H), 7.02-7.05 (m, 1H), 6.78 (s, 1H), 5.69-5.62 (m, 1H), 4.82 (s, 2H), 4.33 (q, J=1.8 Hz, 2H), 4.00 (s, 3H), 1.72 (d, J=1.8 Hz, 3H).

Example 3 Preparation of Substituted Macrocyclic Compound 28

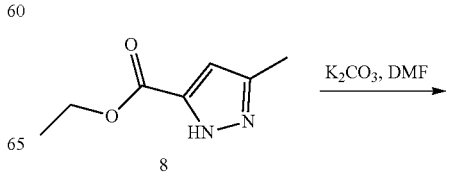

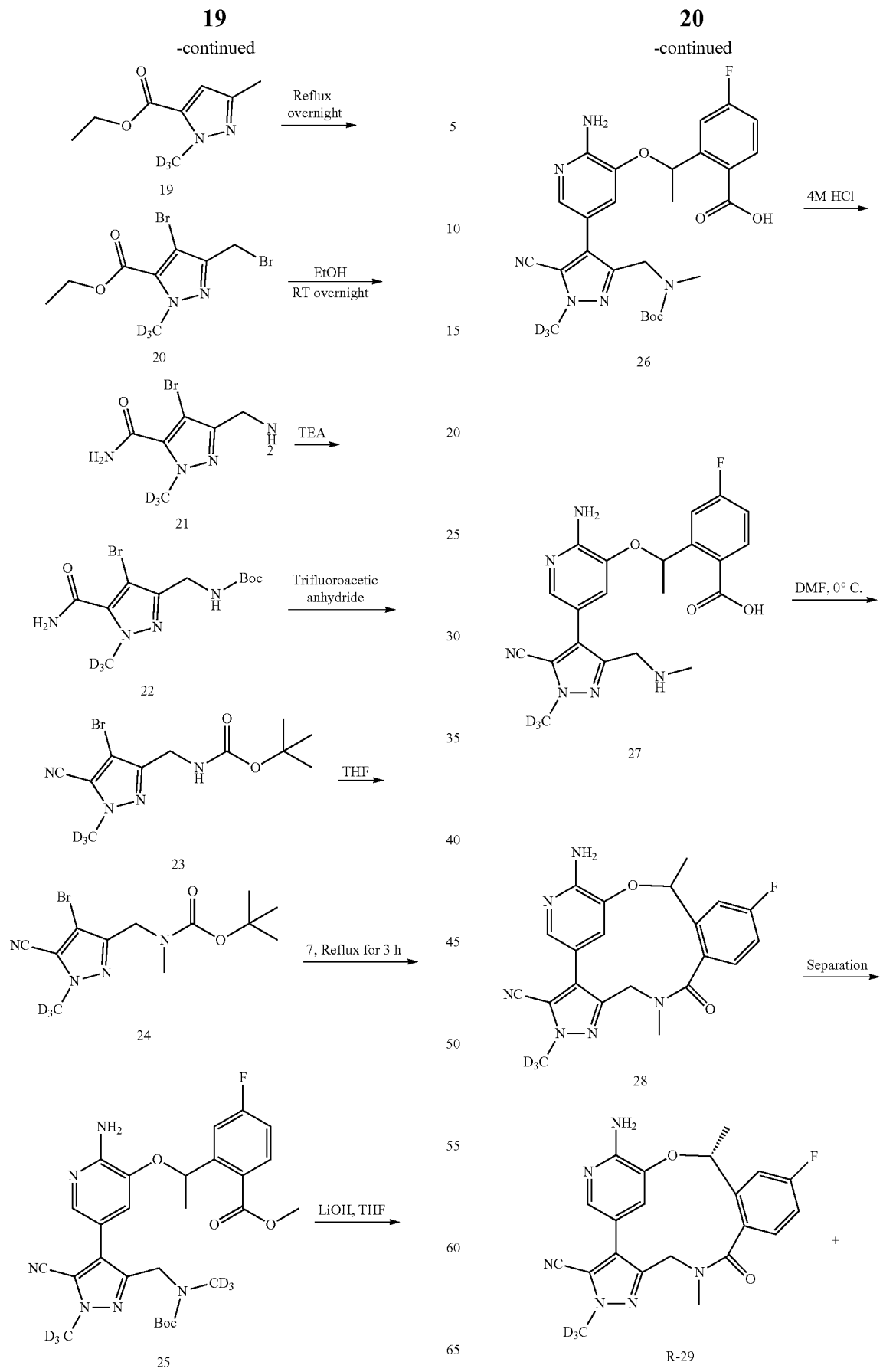

-continued

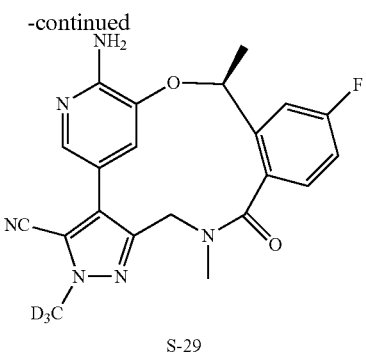

S-29

Step 1 Synthesis of Compound 19.

Under nitrogen protection, compound 8 (3.08 g, 20 mmol), DMF (30 mL), potassium carbonate (5.48 g, 40 mmol), and d3-methyl 4-methylbenzenesulfonate (5.67 g, 30 mmol) were sequentially added to a single-neck round bottom flask, heated to 70° C. and reacted at this temperature for 18 hours. After cooling to room temperature, water was added and the mixture was extracted with dichloromethane. The organic phase was collected and purified by column to obtain 1.6 g of a colorless oily product with a yield of 47%. LC-MS (APCI): m/z=172.1 (M+1)$^+$; $^1$H NMR (400 MHz, CDCl$_3$)(δ ppm): 6.62 (s, 1H), 4.33 (q, J=6.8 Hz, 2H), 2.28 (s, 3H), 4.33 (q, J=6.8 Hz, 3H).

Step 2 Synthesis of Compound 20.

Compound 19 (3.4 g, 20 mmol) and 1,2-dichloroethane (100 mL) were added to a single-neck flask to give a clear solution, and to the stirred solution were added NBS (7.5 g, 42 mmol) and benzoyl peroxide (BPO, 0.64 g, 2.6 mmol). The mixture was heated to reflux overnight, then cooled to room temperature and stirred in an ice bath for 1 hour. After a needle solid appeared, it was filtered, and the filtrate was collected and purified by column to obtain 4.8 g of a white solid with a yield of 73%. LC-MS (APCI): m/z=330 (M+1)$^+$.

Step 3 Synthesis of Compound 21.

Compound 20 (2 g, 6.13 mmol) and ethanol (15 ml) were added to a single-neck flask. After a clear solution was formed, aqueous ammonia (15 ml) was added, stirred at room temperature for 24 hours, and concentrated to give 1.5 g of a yellow solid, which was used directly for the next step. LC-MS (APCI): m/z=236 (M+1)$^+$.

Step 4 Synthesis of Compound 22.

In a continuously stirred two-neck round-bottom flask, compound 21 (1.5 g, 6.13 mmol), N,N-dimethylformamide (DMF, 15 mL) and TEA (1.3 g, 13 mmol) were successively added, followed by dichloromethane. After ventilating, the reaction system was placed under a nitrogen atmosphere. (BOC)$_2$O (2 g, 9 mmol) was added dropwise in an ice-water bath, and the mixture was stirred overnight at room temperature. The reaction was quenched with water and dichloromethane, and extracted with dichloromethane. The organic phase was separated and purified by column to give 600 mg of a white solid product with a yield of 29%. LC-MS (APCI): m/z=336 (M+1)$^+$.

Step 5 Synthesis of Compound 23.

In a continuously stirred three-neck round-bottom flask, compound 22 (1.2 g, 3.6 mmol), dichloromethane (90 mL) and TEA (2.9 g, 28.8 mmol) were successively added, and cooled to −5° C. A solution of trifluoroacetic anhydride (3.8 mg, 18 mmol) in dichloromethane (10 mL) was added dropwise and stirred at 0° C. for 1 hour. The mixture was diluted with dichloromethane, and washed successively with 5% citric acid, sodium bicarbonate solution, and brine. The organic phase was collected and purified by column to give 720 mg of a yellow solid with a yield of 63%. LC-MS (APCI): m/z=318.1 (M+1)$^+$.

Step 6 Synthesis of Compound 24.

Under a nitrogen atmosphere, compound 23 (461 mg, 1.5 mmol) was added to a two-neck round-bottom flask, and tetrahydrofuran (5 mL) was added to give a clear solution, which was cooled to −78° C. Hexamethyldisilazide lithium (LiHMDS, 1.7 ml, 1.7 mmol) was added. After stirring for 30 minutes, CH$_3$I (420 mg, 2.9 mmol) was added, and the mixture was stirred at room temperature for 3 hours after the addition was completed. After adding water and extracting with ethyl acetate, the organic phase was collected and purified by column to obtain 220 mg of a yellow oily product with a yield of 45%. LC-MS (APCI): m/z=332.1 (M+1)$^+$.

Step 7 Synthesis of Compound 25.

Under a nitrogen atmosphere, compound 7 (90 mg, 0.24 mmol), compound 24 (80 mg, 0.24 mmol), bis-pinadol diboron (90 mg, 0.36 mmol), CsF (190 mg, 1.26 mmol) and MeOH/H$_2$O (9:1, 5 mL) were successively added to a two-neck round bottom flask. After uniform stirring, a solution of Pd(OAc)$_2$ (5 mg, 0.024 mmol) in toluene (0.5 mL) was added and heated to 60° C. After refluxing overnight, the mixture was cooled to room temperature, diluted with ethyl acetate and filtered. The filtrate was washed successively with water and brine. The organic phase was collected and purified by column to give 87 mg of a yellow oily product with a yield of 67%. LC-MS (APCI): m/z=542.2 (M+1)$^+$.

Step 8 Synthesis of Compound 26.

To a single-neck round bottom flask was sequentially added compound 25 (200 mg, 0.36 mmol), tetrahydrofuran (5 mL), LiOH.H$_2$O (151 mg, 3.6 mmol) and H$_2$O (5 mL), and stirred overnight at room temperature. Sodium sulfate decahydrate was added, stirred for 5 minutes, dried over anhydrous sodium sulfate, and filtered. The organic phase was collected to afford 180 mg of a brown oil with a yield of 95%. LC-MS (APCI): m/z=528 (M+1)$^+$.

Step 9 Synthesis of Compound 27.

Under a nitrogen atmosphere, compound 15 (180 mg, 0.34 mmol), MeOH (2 mL), and HCl in 1,4-dioxane (2 mL, 3.32 mmol) were added sequentially to a single-neck round bottom flask and heated to 40° C. The mixture was reacted for 2 hours. The solvent was removed, and the residue was purified by column to give 80 mg of a yellow oily product with a yield of 53%. LC-MS (APCI): m/z=428.2 (M+1)$^+$.

Step 10 Synthesis of Compound 28.

2-(7-azobenzotriazole)-N,N,N',N'-tetramethyluronium hexafluorophosphate (HATU, 97 mg, 0.25 mmol) and dry DMF (2 mL) were added sequentially to a single-neck round bottom flask, and cooled to 0° C. Then, a mixed solution of compound 16 (80 mg, 0.18 mmol) and N,N-diisopropylethylamine (DIPEA, 234 mg, 1.4 mmol) in DMF (1 mL) and THF (0.1 mL) was slowly added dropwise into the above round bottom flask at 0° C. After the addition was completed, stirring was continued at this temperature for 30 minutes. After adding water and ethyl acetate to quench the reaction, the organic phase was separated, and extracted with ethyl acetate. The organic phase was collected and purified by column to obtain 20 mg of a white solid compound 28. The racemate compound 28 (20 mg) was separated by chiral supercritical fluid chromatography (SFC) to give the target products R-29 and S-29, 6 mg each. LC-MS (APCI): m/z=410 (M+1)$^+$; $^1$H NMR (300 MHz, CDCl$_3$)(δ ppm) 7.75 (s, 1H), 7.24-7.11 (m, 2H), 7.02-7.05 (m, 1H), 6.78 (s, 1H), 5.69-5.62 (m, 1H), 4.82 (s, 2H), 4.33 (q, J=1.8 Hz, 2H), 3.68 (s, 3H), 1.72 (d, J=1.8 Hz, 3H).

Example 4 Preparation of Substituted Macrocyclic Compound 45
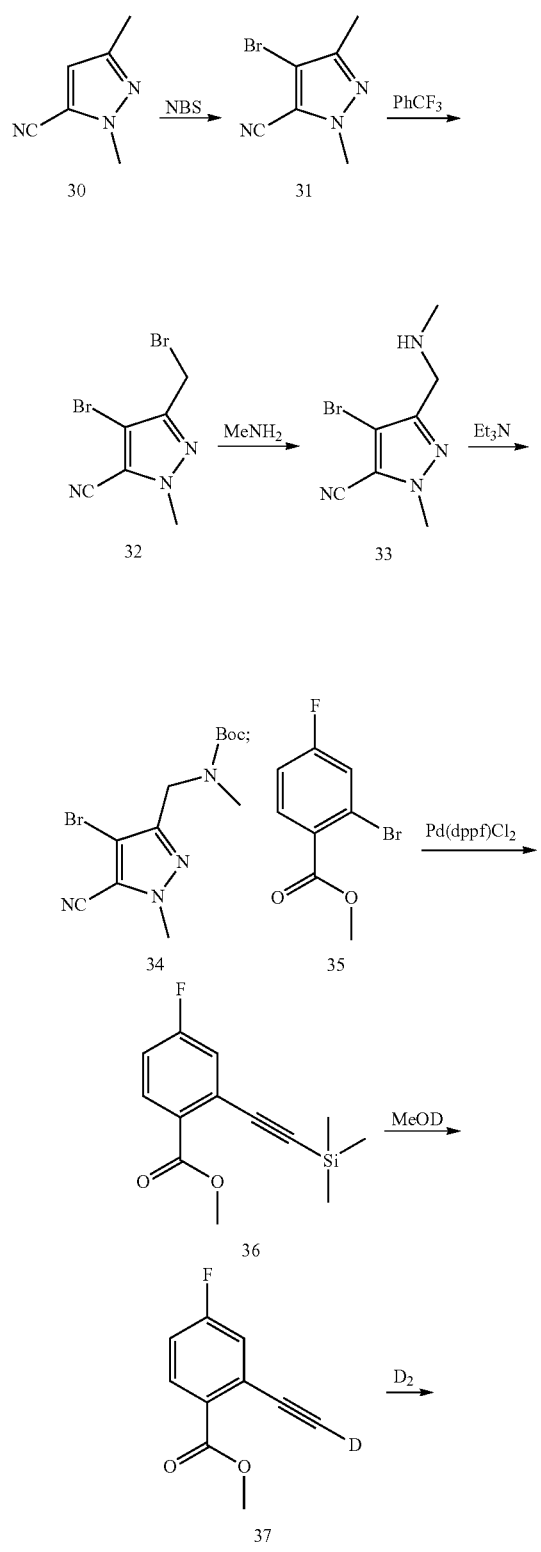
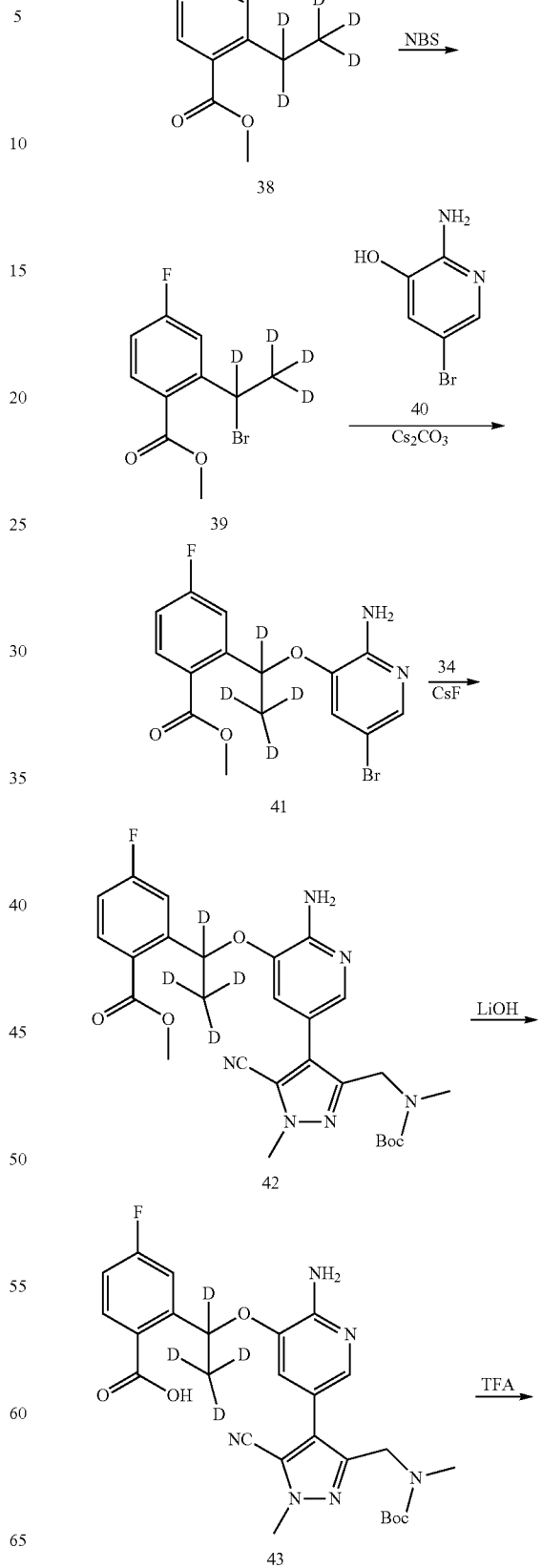

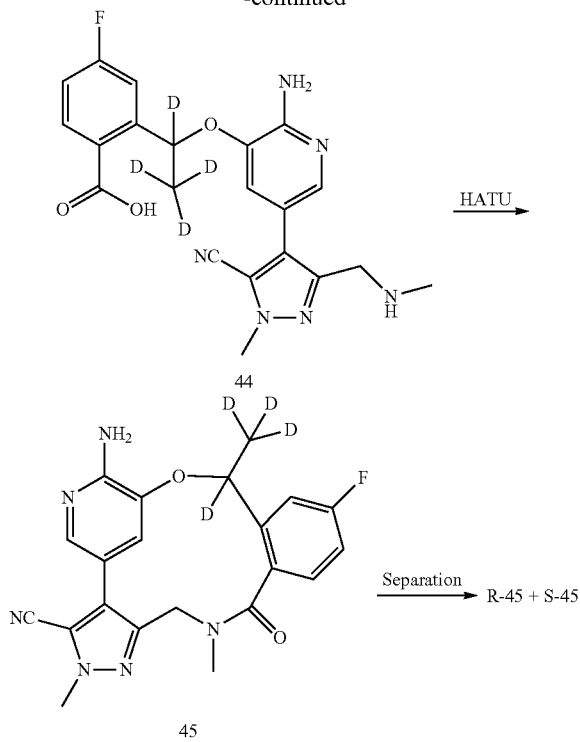

Step 1 Synthesis of Compound 31.

N-bromosuccinimide (NBS, 6.4 g, 36 mmol) was added to a solution of compound 30 (3.6 g, 30 mmol) in acetonitrile and stirred at 90° C. for 3 hours. After cooling to room temperature, the solvent was removed, and the residue was purified by column chromatography to give 5.5 g of a white solid compound 31 with a yield of 91.6%. $^1$H NMR (400 MHz, CDCl$_3$)(δ ppm) 3.99 (s, 3H), 2.27 (s, 3H).

Step 2 Synthesis of Compound 32.

Compound 31 (5.5 g, 27.5 mmol) was dissolved in 60 mL dry trifluorotoluene under a nitrogen atmosphere. After heating to 45° C., NBS (6.85 g, 38.5 mmol) and azobisisobutyronitrile (AIBN, 200 mg) were successively added. After heating to 85° C. for 1 hour, 150 mg AIBN was added again and reacted for 3 hours. After cooling to room temperature, the mixture was filtered, and the organic phase was collected and purified by column to obtain 5.2 g of the title compound 32 with a yield of 67.8%.

Step 3 Synthesis of Compound 34.

Compound 32 (5.2 g, 18.65 mmol) was dissolved in 10 mL of acetonitrile under a nitrogen atmosphere. After the solution was cooled to 0° C., a solution of MeNH$_2$ in tetrahydrofuran (2 M, 40 mL, 80 mmol) was added dropwise to react at room temperature for 1 hour. The solvent was removed. 40 mL of dichloromethane, and then triethylamine (TEA, 3.77 g, 37.2 mmol) were successively added. After cooling to 0° C., Boc$_2$O (5.28 g, 24.18 mmol) was added and the reaction was continued for 30 minutes at room temperature. After adding 10 mL of water and extracting with dichloromethane, the organic phase was separated and purified by column to obtain a total of 5.0 g of compound 34 as a colorless oil with a yield of 81.7%. $^1$H NMR (400 MHz, CDCl$_3$)(δ ppm) 4.45 (d, J=13.6 Hz, 2H), 4.02 (s, 3H), 2.83 (s, 3H), 1.45 (s, 9H).

Step 4 Synthesis of Compound 36.

Under a nitrogen atmosphere, a solution of compound 35 (5 g, 21.46 mmol), PdCl$_2$(PPh$_3$)$_2$ (452 mg, 0.64 mmol), and CuI (41 mg, 0.21 mmol) in 40 mL of triethylamine (TEA) was added dropwise to ethynyltrimethylsilane (2.52 g, 25.75 mmol) and heated to 90° C. for 2 hours. After cooling to room temperature, 50 mL of ethyl acetate was added. After filtration, the filtrate was collected and purified by column to give a totle of 5.3 g of the title compound 36 with a yield of 97%. $^1$H NMR (400 MHz, CDCl$_3$)(δ ppm) 7.97-7.90 (m, 1H), 7.28-7.25 (m, 1H), 7.08-7.04 (m, 1H), 3.92 (s, 3H), 0.28 (s, 9H).

Step 5 Synthesis of Compound 37.

Under a nitrogen atmosphere, potassium carbonate (2.94 g, 21.2 mmol) was added to a solution of compound 36 (5.3 g, 21.2 mmol) in MeOD/CDCl$_3$ (1/1, 20 mL), and stirred at room temperature for 3 hours. The mixture was filtered and the cake was washed with ethyl acetate. The filtrate was collected and purified by column to obtain 3.4 g of the title compound 37 with a yield of 89.6%. $^1$H NMR (400 MHz, CDCl$_3$)(δ ppm) 8.01-7.98 (m, 1H), 7.32 (dd, J=8.8 Hz, 2.4 Hz, 1H), 7.14-7.09 (m, 1H), 3.94 (s, 3H).

Step 6 Synthesis of Compound 38.

Under a deuterium atmosphere, 31 mg of Pd/C was added to a solution of compound 37 (310 mg, 1.73 mmol) in 10 mL of ethyl acetate, stirred at room temperature overnight, and filtered. The filter cake was washed with ethyl acetate, and the filtrate was collected and purified by column to obtain a total of 300 mg of the title compound 38 with a yield of 96.7%.

Step 7 Synthesis of Compound 39.

Under a nitrogen atmosphere, AIBN (126 mg, 0.77 mmol) was added to a solution of compound 38 (4.8 g, 25.67 mmol) and NBS (5.0 g, 28.24 mmol), heated to 80° C. and reacted for 4 hours. After cooling to room temperature, the mixture was filtered. The filter cake was washed with dichloromethane. The filtrate was collected and purified by column to obtain a total of 6.3 g of the title compound 39 with a yield of 84.2%.

Step 8 Synthesis of Compound 41.

Under a nitrogen atmosphere, compound 40 (2.37 g, 12.63 mmol) was added to a solution of compound 39 (3.5 g, 13.25 mmol) and cesium carbonate (4.94 g, 15.12 mmol) in 40 mL of acetonitrile, heated to 50° C. and reacted for 2 hours. After cooling to room temperature, the mixture was filtered, and the cake was washed with dichloromethane and ethyl acetate. The filtrate was collected and purified by column to obtain 2.9 g of the title compound 41 with a yield of 61.7%. $^1$H NMR (400 MHz, CDCl$_3$)(δ ppm) 8.08-8.04 (m, 1H), 7.66 (d, J=1.6 Hz, 1H), 7.24 (dd, J=8.8 Hz, 2.4 Hz, 1H), 7.06-7.01 (m, 1H), 6.75 (d, J=2.4 Hz, 1H), 4.78 (br s, 2H), 3.96 (s, 3H).

Step 9 Synthesis of Compound 42.

Under nitrogen atmosphere, compound 41 (2.3 g, 6.1 mmol), compound 34 (2 g, 6.1 mmol), bis-pinacol diboron (2.32 g, 9.2 mmol), CsF (4.87 g, 32 mmol) and 60 mL of MeOH/H$_2$O (9:1) was added to a round bottom flask. A solution of Pd(OAc)$_2$ (0.14 g, 0.61 mmol) and cataCXium (0.44 g, 1.2 mmol) in toluene (6 mL) were added while stirring at 60° C. The mixture was heated to reflux, and an additional solution of Pd(OAc)$_2$ (0.07 g, 0.31 mmol) and cataCXium (0.22 g, 0.6 mmol) in toluene (6 mL) were added and stirred at 60° C. overnight. After cooling to room temperature, 20 mL of ethyl acetate was added and the mixture was filtered. The filtrate was collected and purified by column to obtain 2.1 g of the title compound 42 with a yield of 63.5%. LC-MS (APCI): m/z=543.2 (M+1)$^+$.

Step 10 Synthesis of Compound 43.

A solution of LiOH.H$_2$O (1.6 g, 38 mmol) in 20 mL of water was added to a solution of compound 42 (2.1 g, 3.87 mmol) in THF, heated to 45° C. and reacted overnight. The organic phase was removed and the solid citric acid was added to adjust the pH of the residue to 5. The mixture was extracted with ethyl acetate. The organic phase was collected and purified by column to obtain a total of 1.2 g of the title compound 43 with a yield of 58.7%. LC-MS (APCI): m/z=529.3 (M+1)$^+$.

Step 11 Synthesis of Compound 44.

To a solution of compound 43 (1.2 g, 2.27 mmol) in 20 mL of dichloromethane was added dropwise trifluoroacetic acid (TFA, 4 mL) under a nitrogen atmosphere at 0° C., and the reaction was carried out at room temperature for 2 hours. Removal of the solvent after drying gave compound 44 which was used directly in the next step. LC-MS (APCI): m/z=429.2 (M+1)$^+$.

Step 12 Synthesis of Compound 45

A round bottom flask containing 2-(7-oxybenzotriazole)-N,N,N',N'-tetramethyluronium hexafluorophosphate (HATU, 601 mg, 1.58 mmol) was filled with nitrogen, 12 mL of anhydrous DMF was added dropwise, and cooled to 0° C. A solution of compound 44 (0.97 g, 2.27 mmol) and N,N-diisopropylethylamine (DIPEA, 3.0 g, 22.7 mmol) in 6 mL of DMF was added, and stirred for 30 minutes at this temperature. 20 mL of water and 20 mL of ethyl acetate were added, and the organic phase was collected and purified by column to obtain 430 mg of the title compound 45 with a yield of 46.2%. The racemate compound 45 (20 mg) was separated using a chiral supercritical fluid chromatography (SFC) to obtain the target products R-45 and S-45. LC-MS (APCI): m/z=411.1 (M+1)$^+$; $^1$H NMR (400 MHz, CDCl$_3$) (δ/ppm) 7.84 (s, 1H), 7.31-7.28 (m, 1H), 7.22-7.19 (m, 1H), 7.02-6.98 (m, 1H), 6.85 (s, 1H), 4.87 (br s, 2H), 4.47-4.34 (m, 2H), 4.07 (s, 3H), 3.13 (s, 3H).

Example 5 Preparation of Substituted Macrocyclic Compound 58

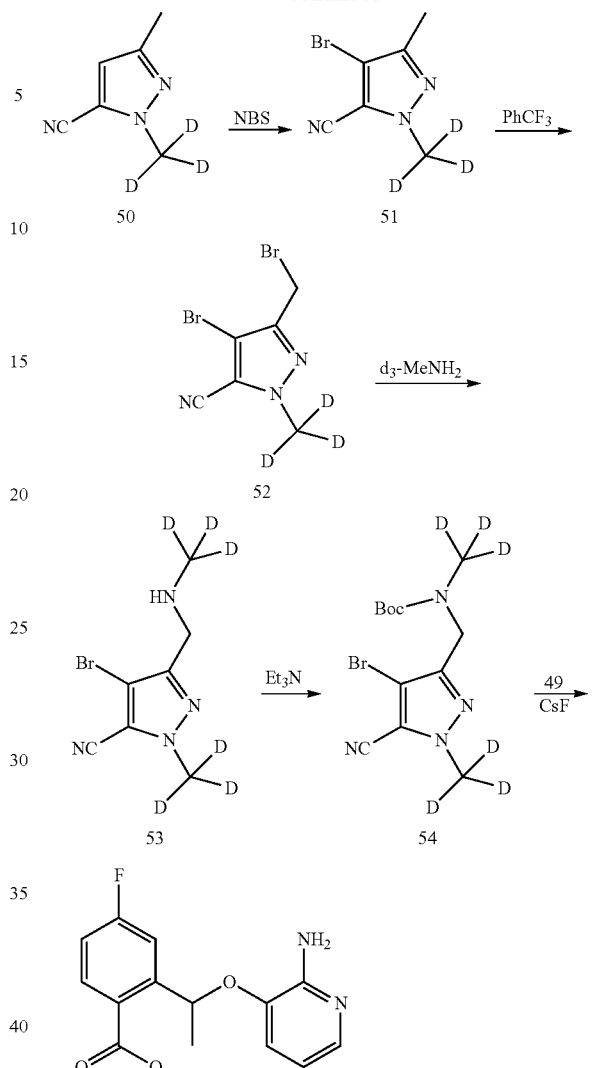

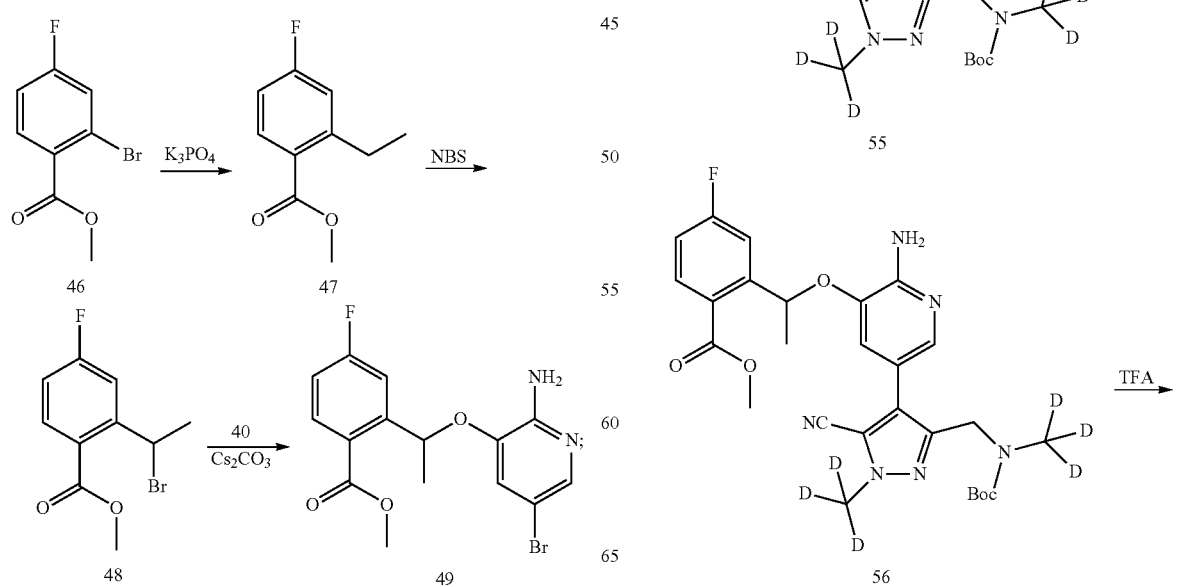

-continued

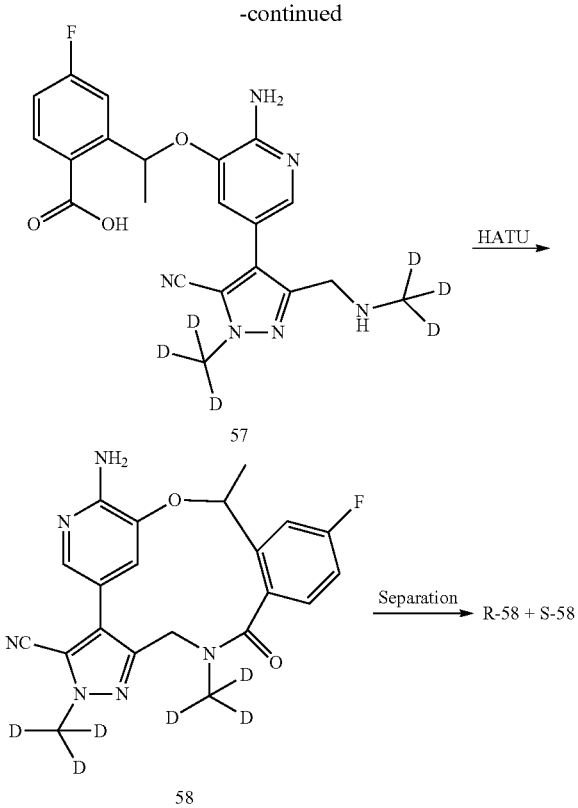

Step 1 Synthesis of Compound 47.

Under a nitrogen atmosphere, a solution of compound 46 (11 g, 47.30 mmol) in 210 mL of toluene was added to 12 mL of water, $K_3PO_4$ (20 g, 94.59 mmol) and ethylboronic acid (7 g, 94.59 mmol), followed by the addition of $Pd(OAc)_2$ (149 mg, 0.66 mmol). The mixture was heated to 100° C., reacted for 3 hours, and then cooled to room temperature. After filteration, the filter cake was washed with ethyl acetate, and the organic phase was collected and purified by column to obtain a total of 8.3 g of the title compound 47 with a yield of 96.6%.

Step 2 Synthesis of Compound 48.

Under a nitrogen atmosphere, NBS (8.93 g, 50.16 mmol) and AIBN (224 mg, 1.37 mmol mmol) were sequentially added to a solution of compound 47 (8.3 g, 45.60 mmol) in 40 mL of $CCl_4$, heated to 80° C. and reacted for 2 hours. After cooling to room temperature, the mixture was filtered, and the filter cake was washed with dichloromethane. The organic phase was collected and purified by column to obtain 8.84 g of the title compound 48 with a yield of 74.5%. $^1$H NMR (400 MHz, $CDCl_3$)(δ ppm) 7.89-7.85 (m, 1H), 7.46 (dd, J=9.6 Hz, 2.4 Hz, 1H), 7.00-6.95 (m, 1H), 6.33 6.27 (m, 1H), 3.90 (s, 3H), 1.97 (d, J=12.0 Hz, 3H).

Step 3 Synthesis of Compound 49.

Under a nitrogen atmosphere, compound 40 (5.81 g, 30.91 mmol) was added to a solution of compound 48 (8.84 g, 34 mmol) and cesium carbonate (12.09 g, 30.91 mmol) in 100 mL of acetonitrile, heated to 50° C. and reacted for 2 hours. After filtration, the filter cake was washed with dichloromethane and ethyl acetate, and the organic phase was collected and purified by column to obtain a total of 9.3 g of the title compound 49, with a yield of 98.8%. $^1$H NMR (400 MHz, $CDCl_3$)(δ ppm) 8.08-8.04 (m, 1H), 7.66 (d, J=1.6 Hz, 1H), 7.24 (dd, J=8.8 Hz, 2.4 Hz, 1H), 7.06-7.01 (m, 1H), 6.75 (d, J=2.4 Hz, 1H), 6.37-6.34 (m, 1H), 4.78 (br s, 2H), 3.96 (s, 3H), 2.04 (d, J=12.0 Hz, 3H).

Step 4 Synthesis of Compound 51.

The specific experimental step is the same as that of Example 4, Step 1, except that compound 50 is used instead of compound 30 to obtain 5.5 g of the title compound 51 with a yield of 91.6%. $^1$H NMR (400 MHz, $CDCl_3$)(δ ppm) 2.27 (s, 3H).

Step 5 Synthesis of Compound 52.

The specific experimental step is the same as that of Example 4, Step 2, except that compound 51 is used instead of compound 31, to obtain a total of 5.2 g of the title compound 52, with a yield of 67.8%. $^1$H NMR (400 MHz, $CDCl_3$)(δ ppm) 4.05 (s, 2H).

Step 6 Synthesis of Compound 54.

The specific experimental step is the same as that of Example 4, Step 3, except that compound 52 is used instead of compound 32, and d3-$MeNH_2$ is used instead of $MeNH_2$, to obtain a total of 0.8 g of the title compound 54 with a yield of 68.7%. $^1$H NMR (400 MHz, $CDCl_3$)(δ ppm) 4.45 (d, J=13.6 Hz, 2H), 1.45 (s, 9H).

Step 7 Synthesis of Compound 55.

The specific experimental step is the same as that of Example 4, Step 9, except that compound 54 is used instead of compound 34 and compound 49 is used instead of compound 41, to obtain a total of 2.1 g of the title compound 55 with a yield of 63.5%. LC-MS (APCI): m/z=545.3 $(M+1)^+$.

Step 8 Synthesis of Compound 56.

The specific experimental step is the same as that of Example 4, Step 10, except that compound 55 is used instead of compound 42, to obtain a total of 1.2 g of the title compound 56 with a yield of 58.7%. LC-MS (APCI): m/z=531.3 $(M+1)^+$.

Step 9 Synthesis of Compound 57.

The specific experimental step is the same as that of Example 4, Step 11, except that compound 56 is used instead of compound 43, to obtain the title compound which was used directly in the next step. LC-MS (APCI): m/z=431.2 $(M+1)^+$.

Step 10 Synthesis of Compound 58.

The specific experimental step is the same as that of Example 4, Step 12, except that compound 57 is used instead of compound 44, to obtain a total of 450 mg of the title compound 58 with a yield of 48.1%. The racemate compound 58 (20 mg) was separated using a chiral supercritical fluid chromatography (SFC) to obtain the target products R-58 and S-58. LC-MS (APCI): m/z=411.1 $(M+1)^+$; $^1$H NMR (400 MHz, $CDCl_3$)(δ/ppm) 7.84 (s, 1H), 7.31-7.28 (m, 1H), 7.22-7.19 (m, 1H), 7.02-6.98 (m, 1H), 6.85 (s, 1H), 5.74-5.72 (m, 1H), 4.87 (br s, 2H), 4.47-4.34 (m, 2H), 1.78 (d, J=6.4 Hz, 3H).

Example 6 Preparation of Substituted Macrocyclic Compound 72

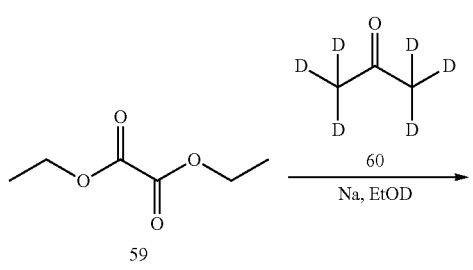

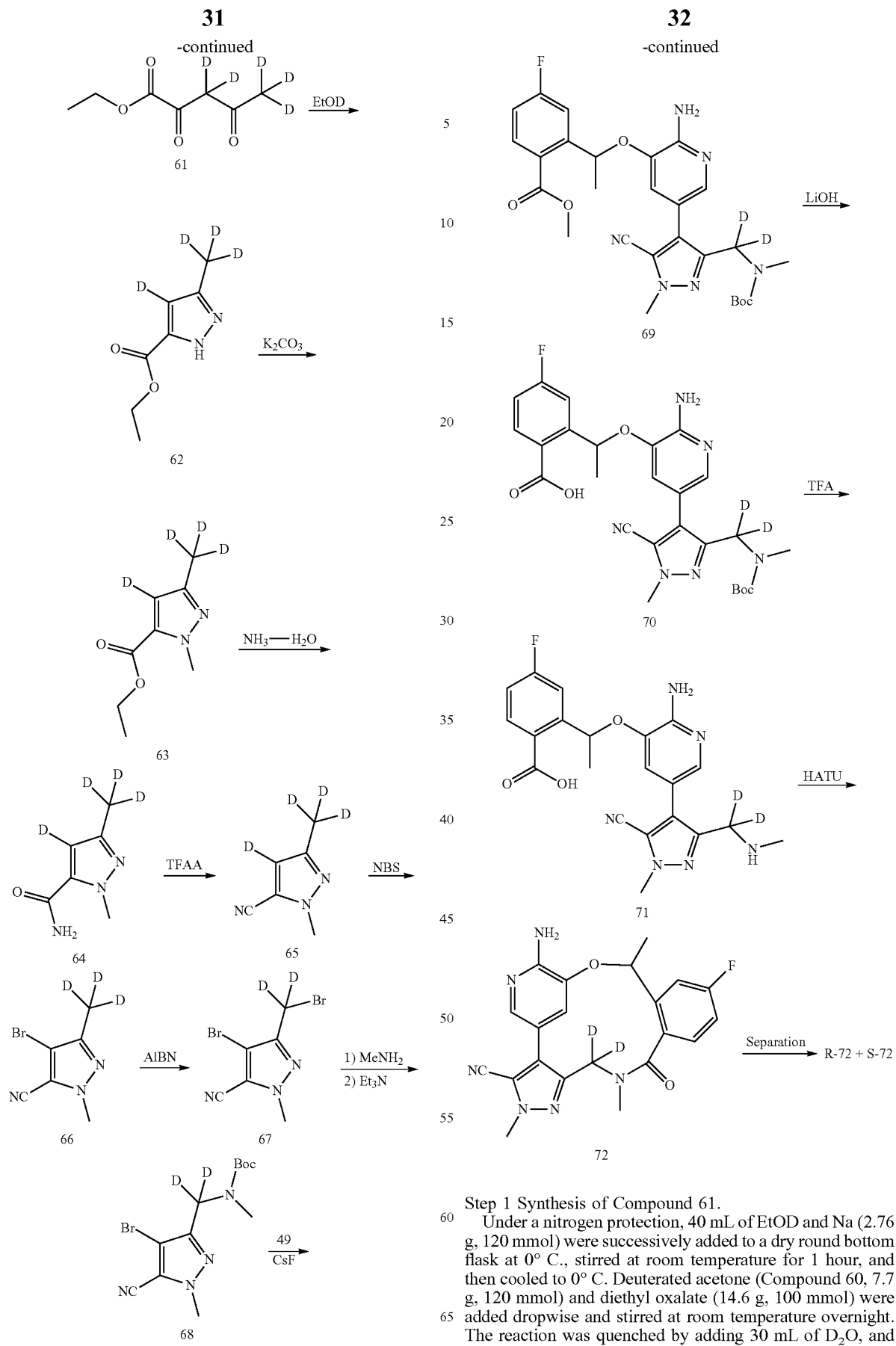

Step 1 Synthesis of Compound 61.

Under a nitrogen protection, 40 mL of EtOD and Na (2.76 g, 120 mmol) were successively added to a dry round bottom flask at 0° C., stirred at room temperature for 1 hour, and then cooled to 0° C. Deuterated acetone (Compound 60, 7.7 g, 120 mmol) and diethyl oxalate (14.6 g, 100 mmol) were added dropwise and stirred at room temperature overnight. The reaction was quenched by adding 30 mL of D₂O, and extracted with ethyl acetate. The organic phase was collected and purified by column to obtain a total of 12 g of the title compound 61 with a yield of 73.6%. LC-MS (ESI): m/z=164.1 (M+1)$^+$.

Step 2 Synthesis of Compound 62.

Under a nitrogen atmosphere, a solution of compound 61 (11 g, 67.4 mmol) in 60 mL of CH$_3$COOD was cooled to 0° C. NH$_2$NH$_2$—H$_2$O (98%, 3.2 g, 64 mmol) in 10 mL of EtOD was added dropwise at that temperature, stirred for 20 minutes, and then heated to 85° C. for 2 hours. After removing the solvent, the residue was purified by column to give a total of 10 g of the title compound 62 with a yield of 95.1%. $^1$H NMR (400 MHz, CDCl$_3$)(δ ppm) 7.24 (br s, 1H), 4.39 (q, J=8.0 Hz, 2H), 1.39 (t, J=8.0 Hz, 3H).

Step 3 Synthesis of Compound 63.

Under a nitrogen atmosphere, 4-methylbenzenesulfonic acid (17.9 g, 96.1 mmol) and potassium carbonate (17.7 g, 128.2 mmol) were added to a solution of compound 62 (10 g, 64.1 mmol) in 150 mL of acetonitrile and heated to 50° C. overnight. After cooling to room temperature, ethyl acetate was added and the mixture was filtered. The filtrate was collected and purified by column to obtain 9 g of the title compound 63 with a yield of 81.5%. LC-MS (APCI): m/z=173.1 (M+1)$^+$.

Step 4 Synthesis of Compound 64.

Compound 63 (9 g, 52.3 mmol) and 100 mL of aqueous ammonia were successively added to a sealed reaction tube, and reacted at room temperature overnight. The mixture was filtered, and washed with water. The filtrate was extracted with dichloromethane. The filter cake was dissolved in an organic phase, dried, collected, and purified by column. A total of 5 g of the title compound 64 was obtained with a yield of 66.8%. LC-MS (APCI): m/z=144.1 (M+1)$^+$.

Step 5 Synthesis of Compound 65.

Under a nitrogen atmosphere, compound 64 (4.8 g, 34.5 mmol), 78 mL of dichloromethane and DIPEA (22.8 mL, 138 mmol) were successively added to a round-bottom flask, and cooled to −10° C. A solution of trifluoroacetic anhydride (TFAA, 5.28 mL, 37.98 mmol) in 12 mL of dichloromethane was slowly added dropwise and stirred at 0° C. for 1 hour after the addition was completed. After the reaction solution was returned to room temperature, the reaction was quenched by adding 50 mL of water. After the extraction with dichloromethane, the organic phase was collected and purified by column to obtain 3.6 g of the title compound 65 with a yield of 87.5%. $^1$H NMR (400 MHz, CDCl$_3$)(δ ppm) 3.98 (s, 3H).

Step 6 Synthesis of Compound 66.

The specific experimental step is the same as that of Example 4, Step 1, except that compound 65 is used instead of compound 30, to obtain 5.5 g of the title compound 66 with a yield of 91.6%. $^1$H NMR (400 MHz, CDCl$_3$)(δ ppm) 3.99 (s, 3H).

Step 7 Synthesis of compound 67.

The specific experimental step is the same as that of Example 4, Step 2, except that compound 66 is used instead of compound 31, to obtain a total of 3.2 g of the title compound 67 with a yield of 41.5%. $^1$H NMR (400 MHz, CDCl$_3$)(δ ppm) 4.05 (s, 3H).

Step 8 Synthesis of Compound 68.

The specific experimental step is the same as that of Example 4, Step 3, except that compound 67 is used instead of compound 32, to obtain 2.6 g of the title compound 68 with a yield of 68.7%. $^1$H NMR (400 MHz, CDCl$_3$)(δ ppm) 4.02 (s, 3H), 2.84 (d, J=15.5 Hz, 3H), 1.44 (s, 9H).

Step 9 Synthesis of compound 69.

The specific experimental step is the same as that of Example 4, Step 9, except that compound 68 is used instead of compound 34 and compound 49 is used instead of compound 41, to obtain 2.1 g of the title compound 69 with a yield of 63.5%. LC-MS (APCI): m/z=541.2 (M+1)$^+$.

Step 10 Synthesis of Compound 70.

The specific experimental step is the same as that in Example 4, Step 10, except that compound 69 is used instead of compound 42, to obtain a total of 1.2 g of the title compound 70 with a yield of 58.7%. LC-MS (APCI): m/z=527.2 (M+1)$^+$.

Step 11 Synthesis of Compound 71.

The specific experimental step is the same as that of Example 4, Step 11, except that compound 56 is used instead of compound 43, to obtain the title compound which was directly used in the next step. LC-MS (APCI): m/z=427.2 (M+1)$^+$.

Step 12 Synthesis of Compound 72.

The specific experimental step is the same as that of Example 4, Step 12, except that compound 57 is used instead of compound 44, to obtain 450 mg of the title compound 72 with a yield of 48.1%. The racemate compound 72 (20 mg) was separated by chiral supercritical fluid chromatography (SFC) to give target products R-72 and S-72. LC-MS (APCI): m/z=408.1 (M+1)$^+$; $^1$H NMR (400 MHz, CDCl$_3$) (δ/ppm) 7.84 (s, 1H), 7.31-7.28 (m, 1H), 7.22-7.19 (m, 1H), 7.02-6.98 (m, 1H), 6.85 (s, 1H), 5.74-5.72 (m, 1H), 4.87 (br s, 2H), 4.07 (s, 3H), 3.13 (s, 3H), 1.78 (d, J=6.4 Hz, 3H).

Example 7 Preparation of Substituted Macrocyclic Compound 76

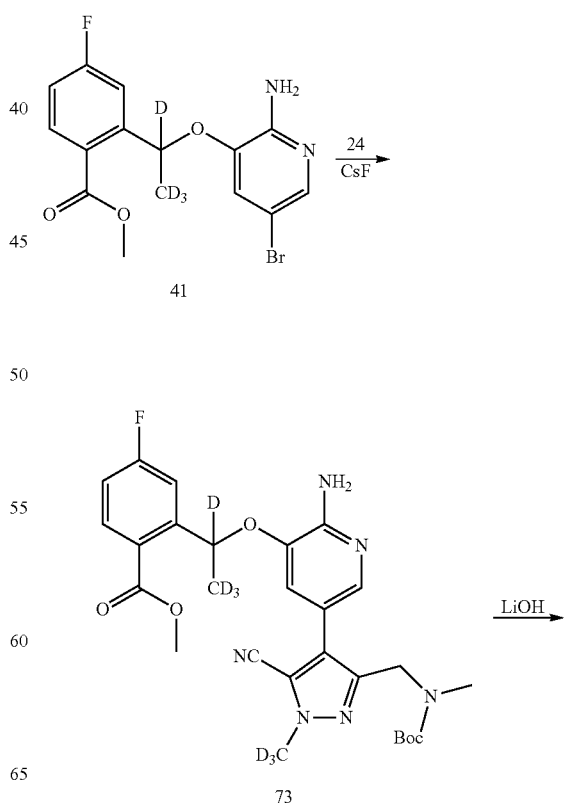

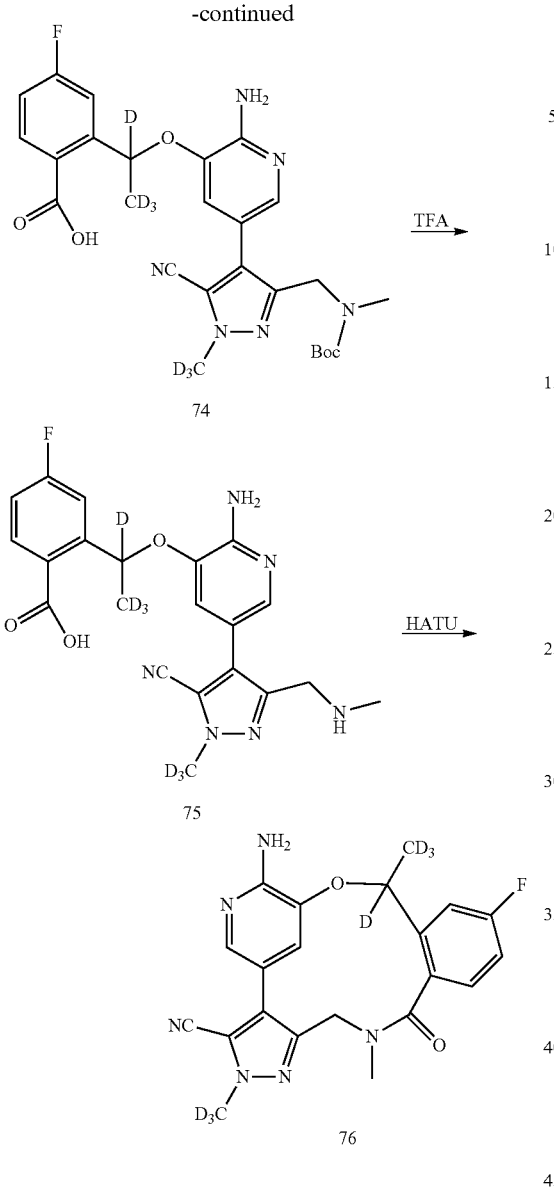

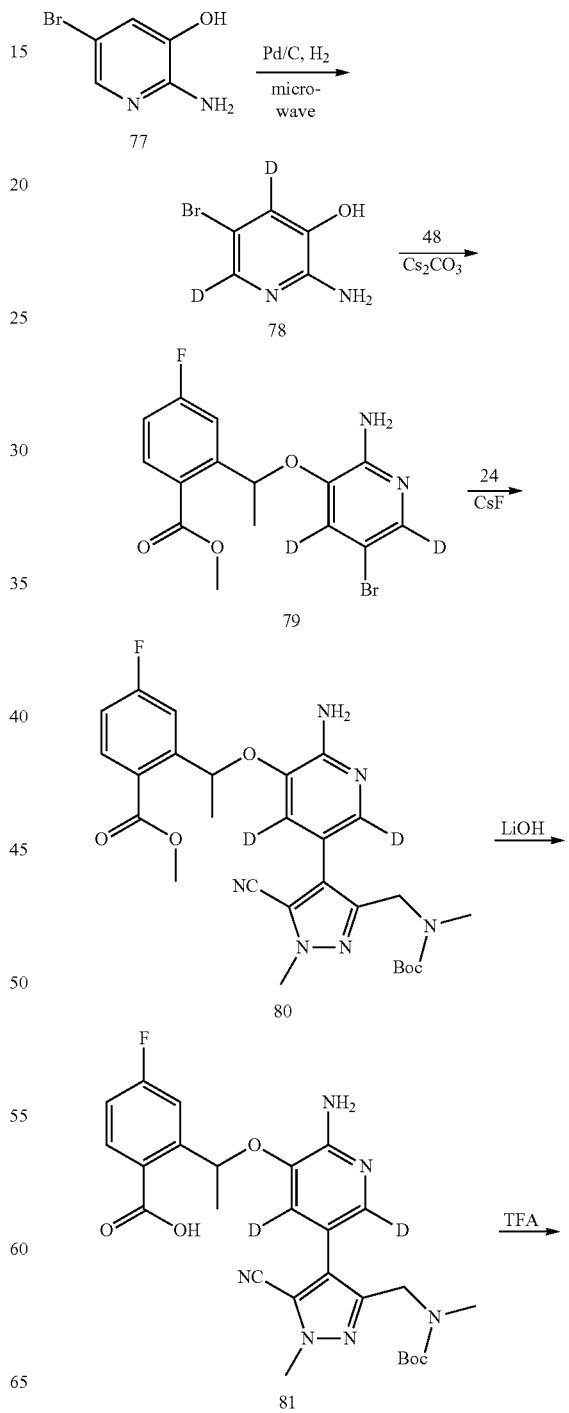

Step 1 Synthesis of Compound 73.

The specific experimental step is the same as that of Example 4, Step 9, except that compound 24 is used instead of compound 34, to obtain 2.1 g of the title compound 73 with a yield of 63.5%. LC-MS (APCI): m/z=546.3 (M+1)$^+$.

Step 2 Synthesis of Compound 74.

The specific experimental step is the same as that in Example 4, Step 10, except that compound 73 is used instead of compound 42, to obtain a total of 1.2 g of the title compound 74 with a yield of 58.7%. LC-MS (APCI): m/z=532.3 (M+1)$^+$.

Step 3 Synthesis of Compound 75.

The specific experimental step is the same as that of Example 4, Step 11, except that compound 74 is used instead of compound 43, to obtain the title compound which is directly used in the next step. LC-MS (APCI): m/z=432.2 (M+1)$^+$.

Step 4 Synthesis of Compound 76.

The specific experimental step is the same as that in Example 4, Step 12, except that compound 75 is used instead of compound 44, to obtain 430 mg of the title compound 76 with a yield of 46.2%. The racemate compound 76 (20 mg) was separated using a chiral supercritical fluid chromatography (SFC) to give the target products R-76 and S-76. LC-MS (APCI): m/z=414.6 (M+1)$^+$; $^1$H NMR (400 MHz, CDCl$_3$)(δ/ppm) 7.84 (s, 1H), 7.31-7.28 (m, 1H), 7.22-7.19 (m, 1H), 7.02-6.98 (m, 1H), 6.85 (s, 1H), 4.87 (br s, 2H), 4.47-4.34 (m, 2H), 3.13 (s, 3H).

Example 8 Preparation of Substituted Macrocyclic Compound 83

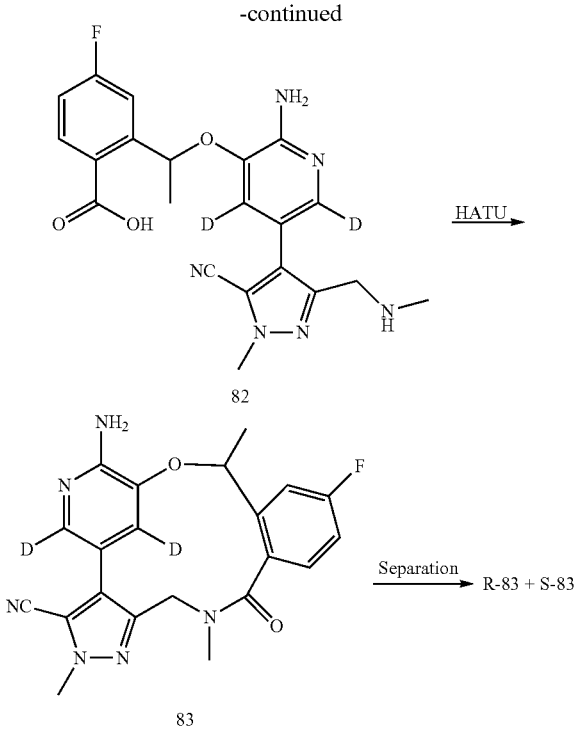

Step 1 Synthesis of Compound 78.

200 mg of Pd/C was added to a solution of compound 77 (2.0 g, 10.64 mmol) in deuterated water (15 mL), bubbled with hydrogen for 5 minutes and then microwaved at 180° C. for 2 hours. After cooling to room temperature, 30 mL of methanol was added. After filtration, the filtrate was collected and dried to obtain 1.85 g of the title compound 78 with a yield of 91.5%. LC-MS (APCI): m/z=191.0 $(M+1)^+$.

Step 2 Synthesis of Compound 79.

Under a nitrogen atmosphere, cesium carbonate (4.22 g, 13 mmol) and compound 48 (2.61 g, 10 mmol) were sequentially added to a solution of compound 78 (1.85 g, 10 mmol) in 30 mL of acetonitrile, heated to 50° C. and reacted for 2 hours. The mixture was filtered, and the filter cake was washed with dichloromethane and ethyl acetate, collected and purified by filtration to obtain 2.15 g of the title compound 79 with a yield of 61.3%. LC-MS (APCI): m/z=371.1 $(M+1)^+$; $^1$H NMR (400 MHz, CDCl$_3$)(δ ppm) 8.06 (dd, J=9.2 Hz, 3.2 Hz, 1H), 7.26 (dd, J=10 Hz, 2.4 Hz, 1H), 7.06-7.04 (m, 1H), 6.36-6.31 (m, 1H), 4.78 (s, 2H), 3.96 (s, 3H), 1.65 (d, J=6.4 Hz, 3H).

Step 3 Synthesis of Compound 80.

The specific experimental step is the same as that of Example 4, Step 9, except that compound 24 is used instead of compound 34 and compound 79 is used instead of compound 41, to obtain 2.1 g of the title compound 73 with a yield of 63.5%. LC-MS (APCI): m/z=541.2 $(M+1)^+$.

Step 4 Synthesis of Compound 81.

The specific experimental step is the same as that of Example 4, Step 10, except that compound 80 is used instead of compound 42, to obtain a total of 1.2 g of the title compound 81 with a yield of 58.7%. LC-MS (APCI): m/z=527.3 $(M+1)^+$.

Step 5 Synthesis of Compound 82.

The specific experimental step is the same as that of Example 4, Step 11, except that compound 81 is used instead of compound 43, to obtain the title compound which is directly used in the next step. LC-MS (APCI): m/z=427.2 $(M+1)^+$.

Step 6 Synthesis of Compound 83.

The specific experimental step is the same as that of Example 4, Step 12, except that compound 82 is used instead of compound 44, to obtain 430 mg of the title compound 83 with a yield of 46.2%. The racemate compound 83 (20 mg) was separated by chiral supercritical fluid chromatography (SFC) to give the target products R-83 and S-83. LC-MS (APCI): m/z=409.2 $(M+1)^+$; $^1$H NMR (400 MHz, CDCl$_3$) (δ/ppm) 7.31-7.28 (m, 1H), 7.22-7.19 (m, 1H), 7.02-6.98 (m, 1H), 5.74-5.72 (m, 1H), 4.87 (br s, 2H), 4.47-4.34 (m, 2H), 4.07 (s, 3H), 3.13 (s, 3H), 1.78 (d, J=6.4 Hz, 3H).

Biological Evaluation of the Compound.

Assay for Inhibition of ALK Tyrosine Kinase Activity.

The inhibition of ALK tyrosine kinase activity can be demonstrated using known methods. For example, in one method, compounds can be tested for their ability to inhibit kinase activity of baculovirus-expressed ALK using a modification of the ELISA protocol reported for trkA in Angeles, T. S. et al., Anal. Biochem. 1996, 236, 49-55, which is incorporated herein by reference. Phosphorylation of the substrate, phopholipase C-gamma (PLC-γ) generated as a fusion protein with glutathione-S-transferase (GST) as reported in rotin, D. et al., EMBO J. 1992, 11, 559-567, which is incorporated by reference, can be detected with europium-labeled anti-phosphotyrosine antibody and measured by time-resolved fluorescence (TRF). In this assay, 96-well plate is coated with 100 μL/well of 10 μg/mL substrate (phospholipase C-γ in tris-buffered saline (TBS). The assay mixture (total volume=100 μL/well) consisting of 20 nM HEPES (pH 7.2, 1 μMATP ($K_m$ level), 5 nM MnCl$_2$, 0.1% BSA, 2.5% DMSO, and various concentrations of test compound is then added to the assay plate. The reaction is initiated by adding the enzyme (30 ng/mL ALK) and is allowed to proceed at 37 degrees C. for 15 minutes. Detection of the phosphorylated product can be performed by adding 100 μL/well of Eu—N1 labeled PT66 antibody (Perkim Elmer # AD0041). Incubation at 37° C. for one hour, followed by addition of 100 μL enhancement solution (for example Wallac #1244-10). The plate is gently agitated and after thirty minutes, the fluorescence of the resulting solution can be measured (for example using EnVision 2100 multilabel plate reader from Perkin Elmer).

Data analysis can then be performed. IC$_{50}$ values can be calculated by plotting percent inhibition versus log$_{10}$ of concentration of compound. The results of the kinase inhibition of the Examples are shown in Table 1, wherein A denotes IC$_{50}$≤1 nM, B denotes IC$_{50}$ of 1-10 nM, C denotes IC$_{50}$ of 10-100 nM, and D denotes IC$_{50}$≥100 nM.

TABLE 1

| Comparison of Kinase Inhibition | | |
|---|---|---|
| Compound No. | ALK WT IC50(nM) | ALK L1196M IC50(nM) |
| Compound 18 | A | B |
| Compound 28 | A | C |
| Compound 45 | A | C |
| Compound 58 | A | C |
| Compound 72 | A | C |
| Compound 76 | A | C |
| Compound 83 | A | C |
| PF-06463922 | A | C |
| Crizotinib | B | C |

As shown in Table 1, compared with the existing ALK inhibitor crizotinib and PF-06463922, the compound disclosed herein showed excellent inhibitory activity against the ALK L1196M mutant ($IC_{50}$ less than 10 nM), indicating that the compound disclosed herein has a strong inhibitory ability against anaplastic lymphoma kinase (ALK).

Cytotoxicity Experiments.

The inhibitory effect of the compound disclosed herein on tumor cells was examined by a tetrazolium salt (MTS) method (Mosman. J. Immunol. Methods. 65: 55-63, 1983). The cell line that can be used in the assay is Ba/F3, a murine pro-B cell line that has been stably transfected with the expression vector pClneo™ (Promega Corp., Madison Wis.) encoding NPM-ALK and subsequently G418-resistant cells were selected. The inhibitory activity of the compounds of Formula I can be determined as follows: BaF3-NPM-ALK cells (15000/well in a microtiter plate) were transferred to a 96-well microtiter plate. Test compounds (dissolved in DMSO) were then added in a series of concentrations (serial dilutions) with a final concentration of DMSO not exceeding 1% (v/v). After addition, the plates were incubated for two days, during which control cultures that did not contain the test compound allowed two cell division cycles. Growth of BaF3-NPM-ALK cells can be measured using Yopro™ staining (T Idziorek et. al., J. Immunol. Methods 1995, 185, 249-258). 25 µL of lysis buffer (consisting of 20 mM sodium citrate, pH 4.0, 26.8 nM sodium chloride, 0.4% NP40, 20 mM EDTA, and 20 mM) was added to each well. The cell lysis was completed at room temperature within 60 minutes and the amount of Yopro bound to the DNA was determined by measurement using, for example, a CytoFluor II 96-well reader (PerSeptive Biosystems). $IC_{50}$ can be determined by computer aided system using the following formula:

$$IC_{50} = [(ABS\ test - ABS\ start)/(ABS\ control - ABS\ start)] \times 100$$

wherein ABS was absorption. The $IC_{50}$ values given in such experiments were the following concentrations of the test compound of interest, which results in a cell number 50% lower than that obtained using a control (without the use of inhibitors).

The experimental results were shown in Table 2, wherein A denotes $IC_{50} \leq 1$ nM, B denotes $IC_{50}$ of 1-100 nM, and C denotes $IC_{50} \geq 100$ nM.

TABLE 2

| Comparison of cytotoxicity | | |
|---|---|---|
| Compound No. | ALK WT IC50(nM) | ALK L1196M IC50(nM) |
| Compound 18 | A | B |
| Compound 28 | A | B |
| Compound 45 | A | B |
| Compound 58 | A | B |
| Compound 72 | A | B |
| Compound 76 | A | B |
| Compound 83 | A | B |
| PF-06463922 | A | B |
| Crizotinib | B | C |

As shown in Table 2, compared to the existing ALK inhibitor crizotinib, the compounds disclosed herein all exhibited excellent anticancer activity that inhibits the growth of cancer cells expressing the ALK mutant L1196M.

Metabolic Experiment of Liver Microparticle.

Experiments in microsomes: Human liver microsomes: 0.5 mg/mL, Xenotech; Rat liver microsomes: 0.5 mg/mL, Xenotech; Coenzyme (NADPH/NADH): 1 mM, Sigma Life Science; Magnesium chloride: 5 mM, 100 mM phosphate buffer (pH 7.4).

Preparation of stock solution: Powder of the example compound 2-8 was accurately weighed and dissolved in DMSO to 5 mM.

Preparation of phosphate buffer (100 mM, pH7.4): A pre-formulated 0.5M potassium dihydrogen phosphate (150 mL) was mixed with 0.5M dibasic potassium phosphate (700 mL). The pH of the mixture was adjusted to 7.4 with 0.5M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH 7.4.

A NADPH regeneration system solution (containing 6.5 mM NADP, 16.5 mM G-6-P, 3 U/mL G-6-PD, 3.3 mM magnesium chloride) was prepared and placed on wet ice prior to use.

Preparation of stop solution: acetonitrile solution containing 50 ng/mL propranolol hydrochloride and 200 ng/mL tolbutamide (internal standard). 25057.5 µL of phosphate buffer (pH 7.4) was taken into a 50 mL centrifuge tube, to which 812.5 µL human liver microsomes were added, and mixed to obtain a liver microsome dilution solution with a protein concentration of 0.625 mg/mL. 25057.5 µL of phosphate buffer (pH 7.4) was taken into a 50 mL centrifuge tube, to which 812.5 µL SD rat liver microsomes were added, and mixed to obtain a liver microsome dilution solution with a protein concentration of 0.625 mg/mL.

Incubation of the samples: The stock solution of the respective compound was respectively diluted to 0.25 mM with an aqueous solution containing 70% acetonitrile, and used as a working solution, ready for use. 398 µL of the dilution solution of human liver microsomes or rat liver microsome were added to a 96-well incubation plate (N=2), respectively, and 2 µL of 0.25 mM working solution was added and mixed.

Metabolic stability assay: 300 µL of pre-chilled stop solution was added to each well of a 96-well deep well plate and placed on ice as a stop plate. The 96 well incubation plate and NADPH regeneration system were placed in a 37° C. water bath box, shaken at 100 rpm and pre-incubated for 5 min. 80 µL of incubation solution was taken out from each well of the incubation plate and added to the stop plate, mixed, and replenished with 20 µL of NADPH regeneration system solution as a 0-min sample. 80 µL of NADPH regeneration system solution was added to each well of the incubation plate to start the reaction and start counting. The corresponding compound had a reaction concentration of 1 µM and the protein concentration was 0.5 mg/mL. Separately, 100 µL of the reaction solution was taken at 10, 30, and 90 min reaction, respectively, added to a stop plate, and vortexed for 3 minutes to terminate the reaction. The stop plate was centrifuged at 5000×g at 4° C. for 4 min. 100 µL of the supernatant was added to a 96-well plate to which 100 µL of distilled water was previously added, mixed, and analyzed by LC-MS/MS.

Data analysis: The peak areas of the corresponding compound and internal standard were detected by LC-MS/MS system, and the ratio of the peak area of the compound to the internal standard was calculated. The slope was measured by plotting the natural logarithm of the percent of compound remaining versus time, and $t_{1/2}$ and $CL_{int}$ were calculated according to the formula below, where V/M is equal to 1/protein concentration.

The compounds disclosed herein were analyzed according to the above procedure and the results are shown in Table 3.

$$t_{1/2} = -\frac{0.693}{\text{Slope}}, \quad CL_{int} = \frac{0.693}{t_{1/2}} \cdot \frac{V}{M}$$

The compound disclosed herein was analyzed according to the above procedure, and the results were shown in Table 3.

TABLE 3

Assessment of metabolism in liver microsomes

| No. | Experiments in human liver microsomes | | Experiments in rat liver microsomes | |
|---|---|---|---|---|
| | $t_{1/2}$ (min) | $CL_{int}$ (μL/min/mg) | $t_{1/2}$ (min) | $CL_{int}$ (μL/min/mg) |
| Compound 18 | >145 | <9.6 | 145 | <9.6 |
| Compound 28 | 142.6 | 9.7 | 145 | <9.6 |
| Compound 45 | >145 | <9.6 | 145 | <9.6 |
| Compound 58 | >145 | <9.6 | 145 | <9.6 |
| Compound 72 | >145 | <9.6 | 145 | <9.6 |
| Compound 76 | >145 | <9.6 | 145 | <9.6 |
| Compound 83 | >145 | <9.6 | 145 | <9.6 |
| PF-06463922 | 117.1 | 11.8 | 145 | <9.6 |

The experimental results show that compared with the existing PF-06463922, the compound disclosed herein exhibits excellent metabolic stability in experiments in both human liver microsome and rat liver microsome.

Pharmacokinetic Experiment in Rats.

Experimental objective: after administration of PF-06463922 or example compounds to rats, the pharmacokinetic behavior of the compounds of the disclosure was investigated.

Experimental Animals:
Species and strains: SD rat grade: SPF grade
Gender and quantity: male, 6
Weight range: 180 to 220 g (the actual weight range was from 187 to 197 g)
Source: shanghai sippr bk laboratory animals ltd.
Experiment Procedure:

Before blood samples were collected, 20 μL of 2 M sodium fluoride solution (esterase inhibitor) was previously added to an EDTA-K2 anticoagulant tube, dried in an 80° C. oven, and placed in a 4° C. refrigerator.

Rats (male, weighing 187 to 197 g) were randomly divided into 2 groups, and were fasted overnight in the afternoon before the experiment but were allowed to drink water freely. Food was given 4 hours after the administration. Group A was given 3 mg/kg of PF-06463922, and group B was given 3 mg/kg of the Example compound. About 100-200 μL of blood was taken from the orbital vein of rats at 15 min, 30 min, 1, 2, 3, 5, 8 and 10 h after administration, placed in a 0.5 mL Eppendorf tube with EDTA-K2 anticoagulant and mixed immediately. After anticoagulation, the tube was gently inverted 5-6 times as quickly as possible. After the blood was taken, it was placed in an ice box, and then within 30 min, the blood sample was centrifuged for 10 min at 4000 rpm and 4° C. to separate the plasma. Immediately after collection of all plasma, it was stored at −20° C. The concentration of the drug in plasma at each time point was determined after sample collection at all time points.

Based on the data of the average concentration of the drug in plasma-time after administration obtained as described above, pharmacokinetics-related parameters of male SD rats after the i.g. administration of PF-06463922 (3 mg/kg) and the Example compound (3 mg/kg) were calculated using the Winnonin software according to non-compartment statistical moment theory.

The experiments showed that, compared with PF-06463922, the compound disclosed herein has better activity and has excellent pharmacokinetic properties, and thus is more suitable as a compound for inhibiting anaplastic lymphoma kinase, and is further suitable for preparing a medicament for treating cancer.

It should be understood that these examples are only for illustrating the present disclosure and are not intended to limit the scope disclosed herein. Experimental methods that do not specify specific conditions in the examples are generally based on conventional conditions or conditions recommended by the manufacturer. Parts and percentages are parts by weight and percentages by weight unless otherwise indicated.

The above content is a further detailed description disclosed herein in combination with specific preferred embodiments, and it cannot be assumed that the specific implementation disclosed herein is limited to these descriptions. For a person of ordinary skill in the art to which the present disclosure belongs, a number of simple deductions or substitutions can be made without departing from the concept disclosed herein, and should all be considered as falling within the protection scope disclosed herein.

What is claimed is:

1. A deuterium-enriched substituted macrocyclic compound, which is a macrocyclic compound represented by formula (I), or a crystal form, a pharmaceutically acceptable salt, a prodrug, a stereoisomer, a hydrate or a solvate thereof,

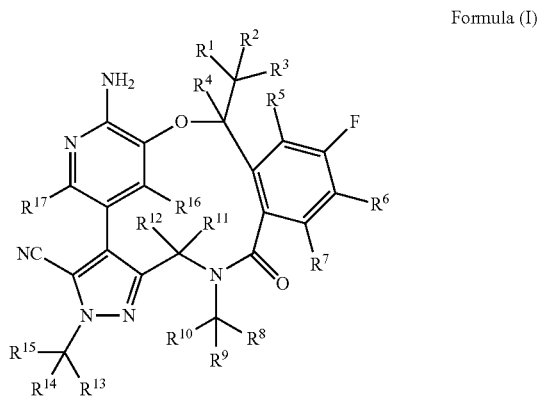

Formula (I)

wherein $R^1$, $R^2$, $R^3$, $R^4$, $R^8$, $R^9$, $R^{10}$, $R^{13}$, $R^{14}$, and $R^{15}$ are each independently hydrogen, deuterium, or halogen; $R^5$, $R^6$, $R^7$, $R^{11}$, $R^{12}$, $R^{16}$, and $R^{17}$ are each hydrogen; provided that at least one of $R^1$, $R^2$, $R^3$, $R^4$, $R^8$, $R^9$, $R^{10}$, $R^{13}$, $R^{14}$, and $R^{15}$ is deuterium.

2. The macrocyclic compound according to claim 1, wherein $R^{13}$, $R^{14}$, and $R^{15}$ are deuterium.

3. The macrocyclic compound according to claim 1, wherein $R^8$, $R^9$, and $R^{10}$ are deuterium.

4. The macrocyclic compound according to claim 2, wherein $R^8$, $R^9$, and $R^{10}$ are deuterium.

5. The macrocyclic compound according to claim 1, wherein $R^1$, $R^2$, $R^3$, and $R^4$ are deuterium.

6. The macrocyclic compound according to claim 2, wherein $R^1$, $R^2$, $R^3$, and $R^4$ are deuterium.

7. The macrocyclic compound according to claim 3, wherein $R^1$, $R^2$, $R^3$, and $R^4$ are deuterium.

8. The macrocyclic compound according to claim 4, wherein $R^1$, $R^2$, $R^3$, and $R^4$ are deuterium.

9. The macrocyclic compound according to claim 1, wherein the compound is selected from the group consisting of the following compounds or pharmaceutically acceptable salts thereof:

Formula (2)
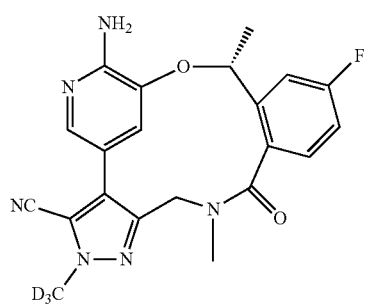

Formula (3)
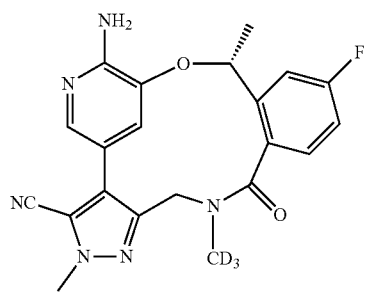

Formula (4)
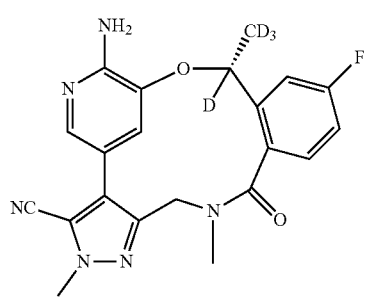

Formula (5)
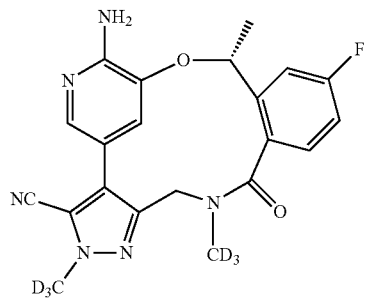

Formula (7)
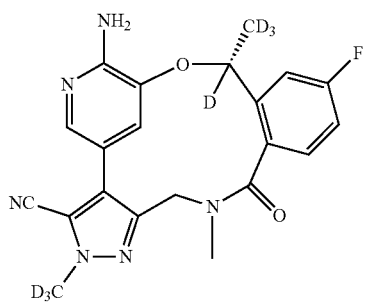

Formula (9)
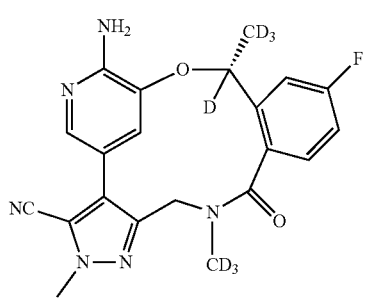

Formula (10)
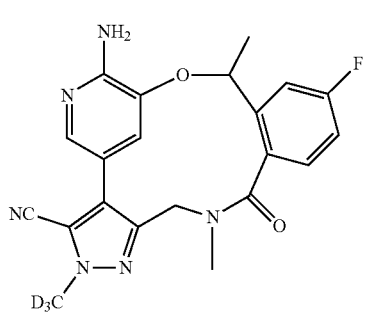

Formula (11)
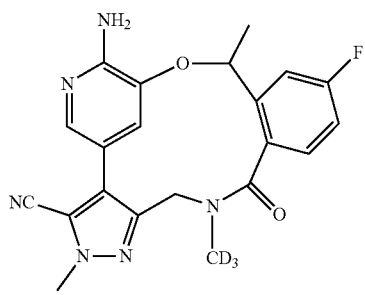

Formula (12)
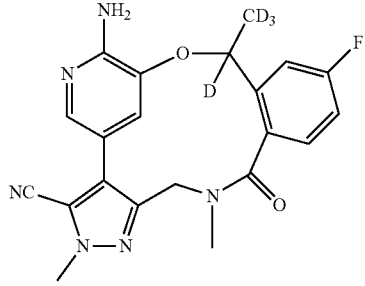

-continued
Formula (13)
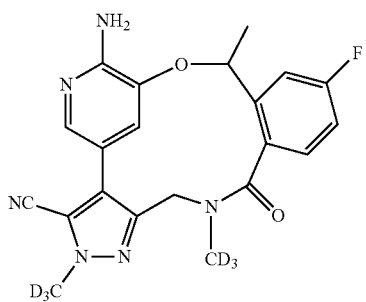
Formula (15)
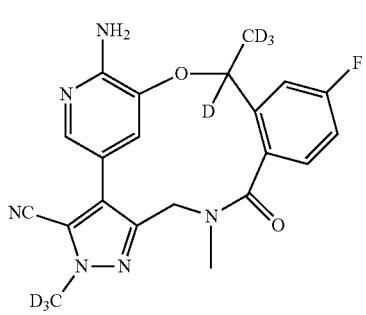
Formula (17)
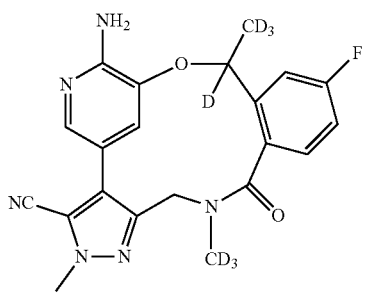
Formula (18)
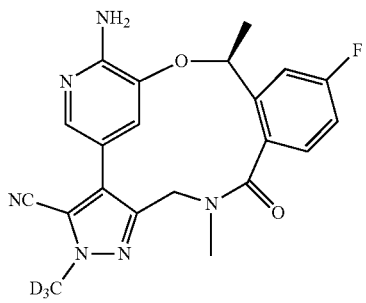
Formula (19)
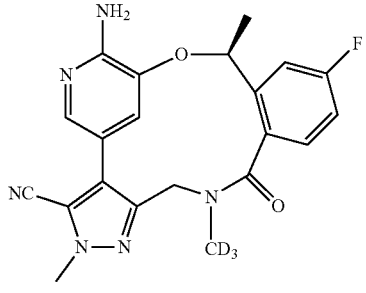
-continued
Formula (20)
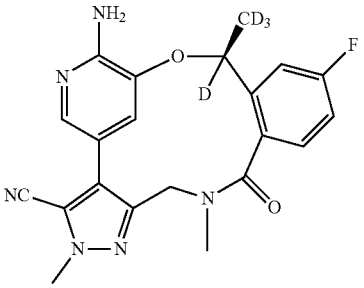
Formula (21)
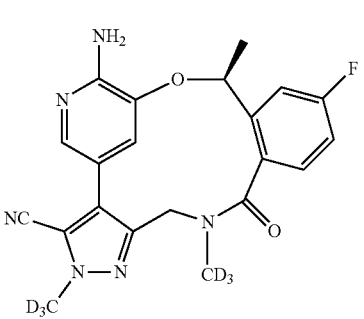
Formula (23)
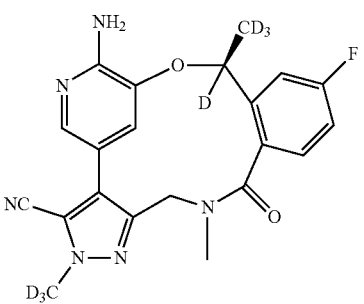
Formula (25)
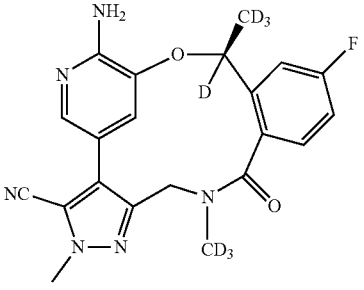
Formula (34)
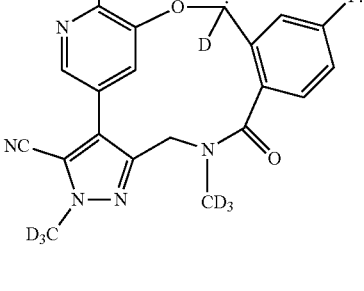

10. The macrocyclic compound according to claim 1, wherein the compound is:

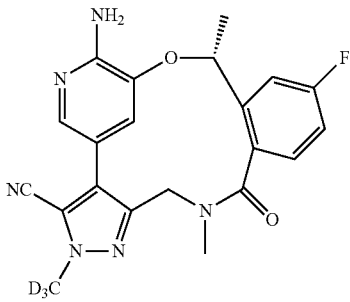 [SMILES: [2H]C([2H])([2H])n1nc2c(c1C#N)-c1cnc(N)c(c1)O[C@H](C)c1cc(F)ccc1C(=O)N(C)C2]

or a pharmaceutically acceptable salt thereof.

11. The macrocyclic compound according to claim 1, wherein the compound is:

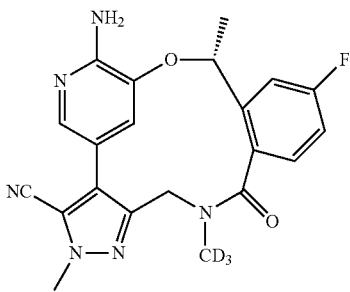 [SMILES: [2H]C([2H])([2H])N1Cc2nn(C)c(C#N)c2-c2cnc(N)c(c2)O[C@H](C)c2cc(F)ccc2C1=O]

or a pharmaceutically acceptable salt thereof.

12. The macrocyclic compound according to claim 1, wherein the compound is:

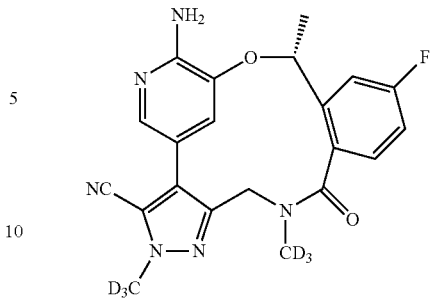

or a pharmaceutically acceptable salt thereof.

13. The macrocyclic compound according to claim 1, wherein the compound is:

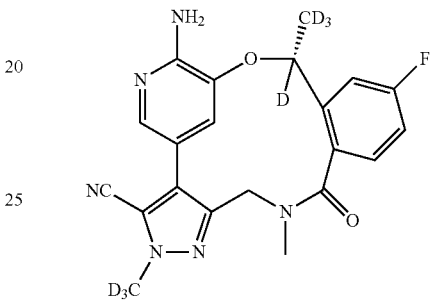

or a pharmaceutically acceptable salt thereof.

14. A pharmaceutical composition, comprising:
a pharmaceutically acceptable carrier, and
the macrocyclic compound according to claim 1, or a crystal form, a pharmaceutically acceptable salt, a hydrate or a solvate, a stereoisomer, a prodrug or an isotopic variant thereof.

15. The pharmaceutical composition according to claim 14, further comprising other therapeutic drugs which are drugs for cancer, cardiovascular disease, inflammation, infection, immune disease, cell proliferative disease, viral disease, metabolic disease, or organ transplant.

16. A method of inhibiting anaplastic lymphoma kinase, comprising administering the macrocyclic compound according to claim 1, or a crystal form, a pharmaceutically acceptable salt, a hydrate or a solvate, a stereoisomer, a prodrug or an isotopic variant thereof.

* * * * *

UNITED STATES PATENT AND TRADEMARK OFFICE
CERTIFICATE OF CORRECTION

PATENT NO. : 10,543,199 B2
APPLICATION NO. : 16/081611
DATED : January 28, 2020
INVENTOR(S) : Yihan Wang et al.

Page 1 of 1

It is certified that error appears in the above-identified patent and that said Letters Patent is hereby corrected as shown below:

On the Title Page

Item (30) Foreign Application Priority Data should read:
Mar. 3, 2016 (CN)............................2016 1 0117814.2

Item (56) References Cited FOREIGN PATENT DOCUMENTS Line 9, delete:
"WO WO 2014/207606 A1 12/2014"

Signed and Sealed this
Seventeenth Day of March, 2020

Andrei Iancu
*Director of the United States Patent and Trademark Office*